(12) United States Patent
Forgacs et al.

(10) Patent No.: US 8,747,880 B2
(45) Date of Patent: Jun. 10, 2014

(54) ENGINEERED BIOLOGICAL NERVE GRAFT, FABRICATION AND APPLICATION THEREOF

(75) Inventors: Gabor Forgacs, Potsdam, NY (US); Stephen H. Colbert, Columbia, MO (US); Bradley A. Hubbard, Columbia, MO (US); Francoise Marga, Columbia, MO (US); Dustin Christiansen, Eugene, OR (US)

(73) Assignee: The Curators of the University of Missouri, Columbia, MO (US)

( * ) Notice: Subject to any disclaimer, the term of this patent is extended or adjusted under 35 U.S.C. 154(b) by 115 days.

(21) Appl. No.: 13/020,000

(22) Filed: Feb. 2, 2011

(65) Prior Publication Data

US 2011/0313542 A1 Dec. 22, 2011

Related U.S. Application Data

(60) Provisional application No. 61/337,307, filed on Feb. 2, 2010, provisional application No. 61/438,097, filed on Jan. 31, 2011.

(51) Int. Cl.
*A61L 27/00* (2006.01)
*A61L 27/58* (2006.01)
*A61B 17/00* (2006.01)

(52) U.S. Cl.
USPC ........... 424/422; 435/368; 435/325; 435/366; 435/347; 424/423; 623/925; 623/23.72

(58) Field of Classification Search
CPC ................. A61B 17/1128; A61B 2017/00004; A61L 27/58; A61L 27/3675; A61L 27/383; A61L 27/3878; A61L 27/3886; C12N 5/0622; C12N 2502/08; C12N 5/0062; C12N 5/0619
USPC .................................. 435/325, 395; 623/1.1
See application file for complete search history.

(56) References Cited

U.S. PATENT DOCUMENTS 4,759,764 A * 7/1988 Fawcett et al. ................. 623/1.1
6,942,830 B2 9/2005 Mülhaupt et al.
(Continued)

FOREIGN PATENT DOCUMENTS

CA 2 306 346 A1 1/1999
EP 2090584 A1 8/2009
(Continued)

OTHER PUBLICATIONS

Harvey et al., Schwann cells and fetal tectal tissue cografted to the midbrain of newborn rats: fate of Schwann cells and their influence on host retinal innervation of grafts. Exp Neurol. Aug. 1995;134(2):179-91.*
(Continued)

*Primary Examiner* — Jeffrey Stucker
*Assistant Examiner* — Aurora M Fontainhas
(74) *Attorney, Agent, or Firm* — Wilson Sonsini Goodrich & Rosati

(57) ABSTRACT

An engineered three-dimensional structure includes living cells cohered with each other. The living cells suitably include Schwann cells and at least one other type of cell. The cells accompanying the Schwann cells can suitably be bone marrow stem cells or another type of cell having one or more anti-inflammatory properties. The structure is suitably a graft that facilitates restorative axon growth when the graft is implanted between the proximal and distal stubs of a severed nerve in a living organism. The graft can optionally include a plurality of acellular conduits extending between opposite axial ends of the graft. Bio-printing techniques can be used to assemble a three-dimensional construct that becomes through maturation an axon-guiding graft, by stacking a plurality of multicellular bodies, each of which includes a plurality of living cells cohered to one another to sufficiently to avoid collapsing when the multicellular bodies are stacked to form the structure.

26 Claims, 19 Drawing Sheets

(56) References Cited

U.S. PATENT DOCUMENTS

| | | | |
|---|---|---|---|
| 6,979,670 | B1 | 12/2005 | Lyngstadaas et al. |
| 7,051,654 | B2 | 5/2006 | Boland et al. |
| 7,625,198 | B2 | 12/2009 | Lipson et al. |
| 8,143,055 | B2 | 3/2012 | Forgacs et al. |
| 8,241,905 | B2 | 8/2012 | Forgacs et al. |
| 2002/0182633 | A1 | 12/2002 | Chen et al. |
| 2002/0188349 | A1 | 12/2002 | McAllister et al. |
| 2003/0049839 | A1* | 3/2003 | Romero-Ortega et al. ... 435/397 |
| 2003/0153078 | A1 | 8/2003 | Libera et al. |
| 2003/0175410 | A1 | 9/2003 | Campbell et al. |
| 2004/0219133 | A1 | 11/2004 | Lyles |
| 2004/0237822 | A1 | 12/2004 | Boland et al. |
| 2004/0253365 | A1 | 12/2004 | Warren et al. |
| 2005/0276791 | A1 | 12/2005 | Hansford et al. |
| 2007/0142916 | A1 | 6/2007 | Olson, Jr. |
| 2007/0231787 | A1 | 10/2007 | Voelker |
| 2008/0070304 | A1 | 3/2008 | Forgacs et al. |
| 2009/0142307 | A1 | 6/2009 | Athanasiou et al. |
| 2009/0208466 | A1 | 8/2009 | Yoo |
| 2009/0248145 | A1 | 10/2009 | Chan |
| 2010/0041134 | A1 | 2/2010 | Forgacs et al. |
| 2011/0212501 | A1 | 9/2011 | Yoo |

FOREIGN PATENT DOCUMENTS

| | | |
|---|---|---|
| WO | 99/01538 A1 | 1/1999 |
| WO | 01/68811 A2 | 9/2001 |
| WO | 2005/081970 A2 | 9/2005 |
| WO | WO-2007-124023 | 11/2007 |
| WO | 2010/008905 A2 | 1/2010 |

OTHER PUBLICATIONS

Wang et al., Bone marrow mesenchymal stem cells promote cell proliferation and neurotrophic function of Schwann cells in vitro and in vivo. Brainresearch 1262 (2009) 7-15.*

Tsang, Three-dimensional Tissue Fabrication, online Jul. 19, 2004, 13 pages, advanced drug delivery reviews.

Baltich, J., et al., "Development of a Scaffoldless Three-Dimensional Engineered Nerve Using a Nerve-Fibroblast Co-Culture," In Vitro Cell. Dev. Biol.—Animal, 2010, pp. 438-444, vol. 46.

Constans, A., "Body by Science," The Scientist, Oct. 6, 2003, vol. 17, No. 19, http://www.the-scientist.com/article/display/14154/, 7 pages.

Dai, W., et al., "Fibroblast Aggregation by Suspension with Conjugates of Poly(ethylene glycol) and RGD," Biotechnology and Bioengineering, May 20, 1996, pp. 349-356, vol. 50, No. 4.

Eisenberg, C. A., et al., "Bone Marrow Cells Transdifferentiate to Cardiomyocytes When Introduced into the Embryonic Heart," Stem Cells, 2006, pp. 1236-1245, vol. 24.

Forgacs, G., et al., "Viscoelastic Properties of Living Embryonic Tissues: A Quantitative Study," Biophysical Journal, May 1998, pp. 2227-2234, vol. 74, No. 5.

Foty, R. A., et al., "Surface Tensions of Embryonic Tissues Predict Their Mutual Envelopment Behavior," Development, 1996, pp. 1611-1620, vol. 122, No. 5.

Foty, R. A., et al., "The Differential Adhesion Hypothesis: A Direct Evaluation," Developmental Biology, 2005, pp. 255-263, vol. 278, vol. 1.

Furukawa, K. S., et al., "Formation of Human Fibroblast Aggregates (Spheroids) by Rotational Culture," Cell Transplantation, 2001, pp. 441-445, vol. 10, No. 4-5.

Furukawa, K. S., et al., "Tissue-engineered Skin Using Aggregates of Normal Human Skin Fibroblasts and Biodegradable Material," J. Artif. Organs, 2001, pp. 353-356, vol. 4.

Glazier, J. A., et al., "Simulation of the Differential Adhesion Driven Rearrangement of Biological Cells," Physical Review E, Mar. 1993, pp. 2128-2154, vol. 47, No. 3.

Glicklis, R., et al., "Modeling Mass Transfer in Hepatocyte Spheroids Via Cell Viability, Spheroid Size, and Hepatocellular Functions," Biotechnology and Bioengineering, Jun. 20, 2004, pp. 672-680, vol. 86, No. 6.

Graner, F., et al., "Simulation of Biological Cell Sorting Using a Two-Dimensional Extended Potts Model," Physical Review Letters, Sep. 28, 1992, pp. 2013-2016, vol. 69, No. 13.

Guenard, V., et al., "Syngeneic Schwann Cells Derived from Adult Nerves Seeded in Semipermeable Guidance Channels Enhance Peripheral Nerve Regeneration," The Journal of Neuroscience, Sep. 1992, pp. 3310-3320, vol. 12, No. 9.

Hadlock, T., et al., "A Polymer Foam Conduit Seeded with Schwann Cells Promotes Guided Peripheral Nerve Regeneration," Tissue Engineering, 2000, pp. 119-127, vol. 6, No. 2.

Hubbard, B. A., et al., "Bioengineered, Autologous, Scaffold-free Nerve Conduit for Peripheral Nerve Repair," Abstract, AAHS/ ASPN/ASRM 2011, Annual Scientific Meetings Program Book, Jan. 12-18, 2011, pp. 140 and 159.

Jakab, K., et al., "Relating Cell and Tissue Mechanics: Implications and Applications," Developmental Dynamics, 2008, pp. 2438-2449, vol. 237.

Jakab, K., et al., "Tissue Engineering by Self-Assembly of Cells Printed into Topologically Defined Structures," Tissue Engineering: Part A, Nov. 3, 2008, pp. 413-421, vol. 14.

Kelm, J. M., et al., "Microscale Tissue Engineering Using Gravity-Enforced Cell Assembly," Trends in Biotechnology, Apr. 2004, pp. 195-202, vol. 22, No. 4.

Koibuchi, N., et al., "Behavior of Cells in Artificially Made Cell Aggregates and Tissue Fragments after Grafting to Developing Hind Limb Buds in *Xenopus laevis*," The International Journal of Developmental Biology, 1999, pp. 141-148, vol. 43, No. 2.

Korff, T., et al., "Blood Vessel Maturation in a 3-Dimensional Spheroidal Coculture Model: Direct Contact with Smooth Muscle Cells Regulates Endothelial Cell Quiescence and Abrogates VEGF Responsiveness," The FASEB Journal, Feb. 2001, pp. 447-457, vol. 15.

Marga, F., et al., "Bioprint Engineered Fully Biological Nerve Graft," Abstract, TERMIS, Dec. 5-8, 2010, Orlando, Florida, 1 page.

Marga, F., et al., "Bioprinted Fully Biological Nerve Graft," Poster Presentation, TERMIS, Dec. 5-8, 2010, Orlando, Florida, 1 page.

Marga, F. S., et al., "Construction of a Bioprinted Fully Biological Nerve Graft," Abstract, Biophysical Journal, Feb. 2009, p. 643a, vol. 96, No. 3, Supplement 1.

Marga, F., et al., "Engineered Fully Biological Nerve Graft," Poster Presentation, Biophysical Society Meeting, Mar. 4, 2009, 1 page.

Marga, F., et al., "Developmental Biology and Tissue Engineering," Birth Defects Research (Part C), 2007, pp. 320-328, vol. 81.

Marga, F., et al., "Engineered Fully Biological Nerve Graft," Oral Presentation, International Conference on Biofabrication, Oct. 3-6, 2010, Philadelphia, Pennsylvania, 1 page.

Martin, I., et al., "Computer-Based Technique for Cell Aggregation Analysis and Cell Aggregation in In Vitro Chondrogenesis," Cytometry, 1997, pp. 141-146, vol. 28, No. 2.

Mironov, V., et al., "Organ Printing: Computer-Aided Jet-Based 3D Tissue Engineering," TRENDS in Biotechnology, Apr. 2003, pp. 157-161, vol. 21, No. 4.

Mironov, V., et al., "Organ Printing: Self-Assembling Cell Aggregates as 'Bioink'," Science & Medicine, Apr. 2003, pp. 69-71, vol. 9, No. 2.

Mironov, V., et al., "Organ Printing: Tissue Spheroids as Building Blocks," Biomaterials, 2009, pp. 2164-2174, vol. 30.

Mizumoto, H., et al., "Formation of Cylindrical Multicellular Aggregate (Cylindroid) and Express of Liver Specific Functions of Primary Rat Hepatocytes," Cytotechnology, 1999, pp. 69-75, vol. 31.

Mombach, J. C. M., et al., "Quantitative Comparison Between Differential Adhesion Models and Cell Sorting in the Presence and Absence of Fluctuations," Physical Review Letters, Sep. 11, 1995, pp. 2244-2247, vol. 75, No. 11.

Nickerson, C. A., et al., "Three-Dimensional Tissue Assemblies: Novel Models for the Study of *Salmonella enterica* Serovar Typhimurium Pathogenesis," Infection and Immunity, Nov. 2001, pp. 7106-7120, vol. 69, No. 11.

Ryan, P. L., et al., "Tissue Spreading on Implantable Substrates is a Competitive Outcome of Cell-Cell vs. Cell-Substratum Adhesivity," Proceedings of the National Academy of Sciences, Apr. 10, 2001, pp. 4323-4327, vol. 98, No. 8.

(56) References Cited

OTHER PUBLICATIONS

"Sciperio, Inc. 2003 R&D 100 Award Winner," Sciperio, http://www.sciperio.com/news/20031016.asp, accessed on Feb. 1, 2005, 2 pages.

Siemionow, M., et al., "Current Techniques and Concepts in Peripheral Nerve Repair," Chapter 8, International Review of Neurobiology, 2009, pp. 141-172, vol. 87.

Steinberg, M. S., "Does Differential Adhesion Govern Self-Assembly Processes in Histogenesis? Equilibrium Configurations and the Emergence of a Hierarchy Among Populations of Embryonic Cells," The Journal of Experimental Zoology, Apr. 1970, pp. 395-433, vol. 173, No. 4.

Steinberg, M. S., et al., "Liquid Behavior of Embryonic Tissues," Cell Behaviour, 1982, pp. 583-697.

Stiles, E., "UA Wins R & D 100 Award for Machine that Prints Tissue Cell-by-Cell," UANews, Dec. 2, 2003, http://uanews.org/cgi-bin/WebObjects/UANews.woa/wa/goPrint?ArticleID=8305, accessed on Feb. 1, 2005, 2 pages.

Timmins, N. E., et al., "Hanging-Drop Multicellular Spheroids as a Model of Tumour Angiogenesis," Angiogenesis, 2004, pp. 97-103, vol. 7, No. 2.

Yamauchi, N., et al., "A Three-Dimensional Cell Culture Model for Bovine Endometrium: Regeneration of a Multicellular Spheroid Using Ascorbate," Placenta, 2003, pp. 258-269, vol. 24.

Kelm, J. M., et al., "Design of Custom-Shaped Vascularized Tissues Using Microtissue Spheriods as Minimal Building Units," Tissue Engineering, 2006, pp. 2151-2160, vol. 12, No. 8.

Norotte, C., et al., "Scaffold-Free Vascular Tissue Engineering Using Bioprinting," Biomaterials, 2009, pp. 5910-5917, vol. 30.

Remuzzi, A., et al., "Vascular Smooth Muscle Cells on Hyaluronic Acid: Culture and Mechanical Characterization of an Engineered Vascular Construct," Tissue Engineering, 2004, pp. 699-710, vol. 10, No. 5/6.

Edelman, E.R. "Vascular Tissue Engineering: Designer Arteries." Circ Res, 1999, 85(12):1115-1117.

Jakab et al. "Engineering Biological Structures of Prescribed Shape Using Self-assembling Multicellular Systems." Proc. Natl. Acad. Sci. USA, 2004, 101:2864-2869.

Lee et al. "Multi-layered Culture of Human Skin Fibroblasts and Keratinocytes Through Three-dimensional Freeform Fabrication." *Biomaterials*, 2009, 30:1587-1595.

Mironov et al. "Bioprinting Living Structures." *J. Mat. Chem.*, 2007, 17:2054-2060.

Niklason and Langer. "Advances in Tissue Engineering of Blood Vessels and Other Tissues." *Transpl. Immunol.*, 1997, 5(4):303-306.

Perez-Pomares and Foty. "Tissue Fusion and Cell Sorting in Embryonic Development and Disease: Biomedical Implications." *Bioessays*, 2006, 28:809-821.

\* cited by examiner

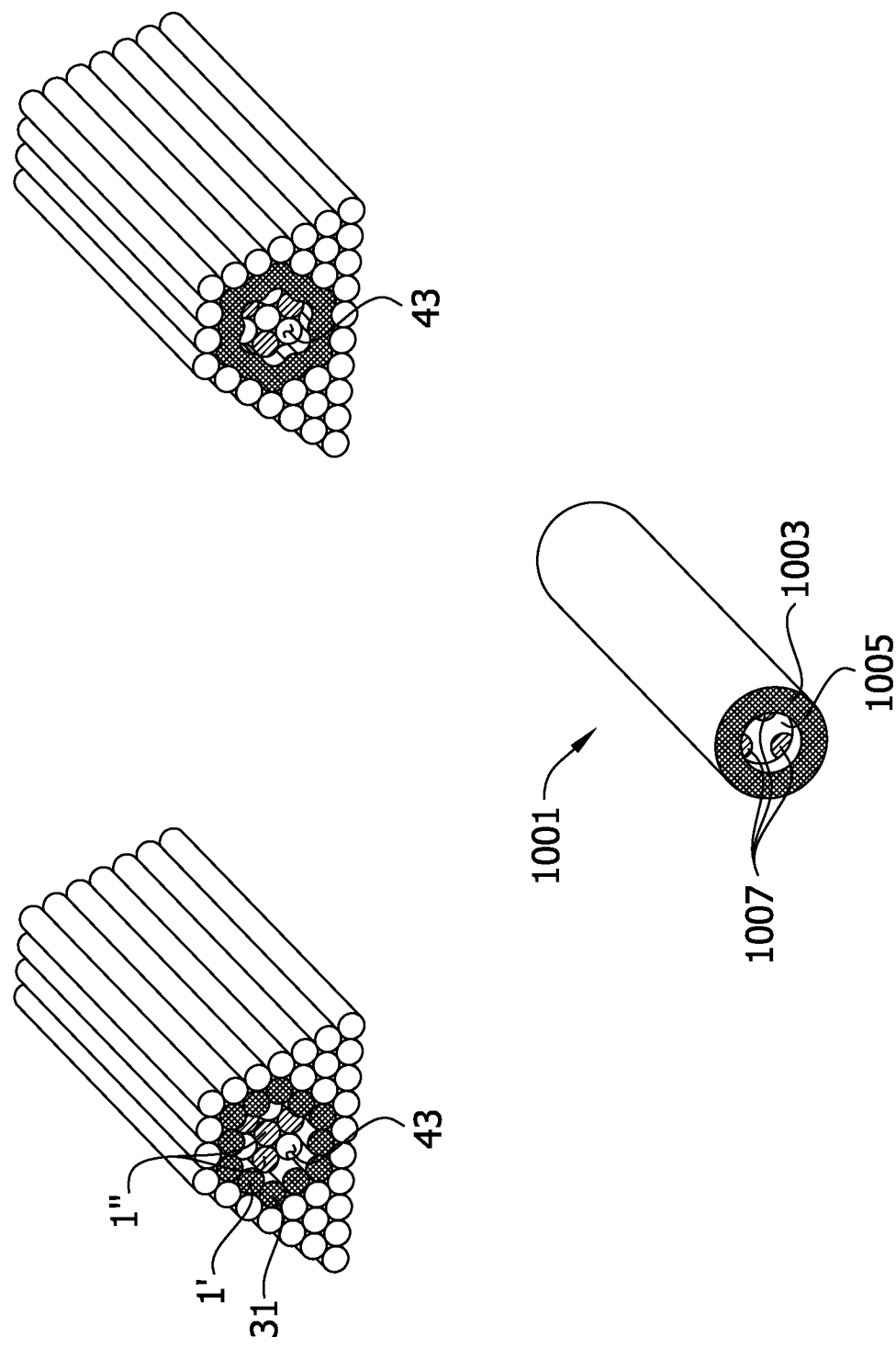

1017   1017   1019

ENGINEERED BIOLOGICAL NERVE GRAFT, FABRICATION AND APPLICATION THEREOF

CROSS-REFERENCE TO RELATED APPLICATIONS

This application claims the benefit of U.S. Provisional Application No. 61/337,307, filed on Feb. 2, 2010, the entirety of which is incorporated by reference herein. This application also claims the benefit of U.S. Provisional Application No. 61/438,097, filed on Jan. 31, 2011, the entirety of which is incorporated by reference herein.

GRANT STATEMENT

This invention was made with government support under Grant No. 0526854 awarded by the National Science Foundation. The government has certain rights in the invention.

FIELD OF THE INVENTION

The present invention relates to the field of regenerative medicine and tissue engineering, and more particularly to the production of axon-guiding grafts and the use thereof for the repair of damaged nerves.

BACKGROUND

A nerve is an enclosed, cable-like bundle of axons. A nerve provides a common pathway for the electrochemical nerve impulses that are transmitted along each of the axons. Each nerve contains many axons. Each axon is surrounded by a layer of connective tissue called the endoneurium. The axons are bundled together into groups called fascicles, and each fascicle is wrapped in a layer of connective tissue called the perineurium. Finally, the entire nerve is wrapped in a layer of connective tissue called the epineurium.

When a nerve axon is severed, the end still attached to the cell body is labeled the proximal segment, while the other end is called the distal segment. Neuroregeneration in the peripheral nervous system (PNS) occurs by axonal sprouts forming at the proximal stump and growing until they reach the distal stump. The growth of the sprouts are governed by chemotactic factors secreted from Schwann cells (neurolemmocytes). The proximal axons are able to regrow as long as the cell body is intact, and they have made contact with the Schwann cells in the endoneurial channel. Human axon growth rates can reach 2 mm/day in small nerves and 5 mm/day in large nerves. The distal segment, however, experiences Wallerian degeneration within hours of the injury; the axons and myelin degenerate, but the endoneurium remains. In the later stages of regeneration the remaining endoneurial tube directs axon growth back to the correct targets. During Wallerian degeneration, Schwann cells grow in ordered columns along the endoneurial tube, creating a band of Bungner (boB) that protects and preserves the endoneurial channel. Also, macrophages and Schwann cells release neurotrophic factors that enhance re-growth.

SUMMARY OF THE INVENTION

One aspect of the invention is a multicellular construct. The construct includes a multicellular region having a plurality of living cells cohered to one another to form an elongate graft for restoring neural connection between the ends of a severed nerve. A plurality of acellular channels extend axially through the interior of the graft.

Another aspect of the invention is an elongate three-dimensional structure. The structure includes a plurality of engineered multicellular bodies. Each multicellular body includes a plurality of living cells cohered to one another. The structure also includes a plurality of discrete filler bodies. Each filler body includes a biocompatible material that resists migration and ingrowth of cells from the multicellular bodies into the filler bodies. The multicellular bodies are arranged in a pattern in which each multicellular body contacts at least one other multicellular body and the filler bodies are positioned and arranged to form a plurality of acellular channels extending between opposite ends of the structure.

Yet another aspect of the invention is an elongate three-dimensional structure. The structure includes a plurality of non-innervated multicellular bodies. Each multicellular body includes a plurality of living cells cohered to one another. The structure includes a plurality of discrete filler bodies. Each filler body includes a biocompatible material that resists migration and ingrowth of cells from the multicellular bodies into the filler bodies. The multicellular bodies are arranged in a pattern in which each multicellular body contacts at least one other multicellular body and the filler bodies are positioned and arranged to form a plurality of acellular channels extending between opposite ends of the structure.

Still another aspect of the invention is an elongate three-dimensional structure. The structure includes a plurality of multicellular bodies. Each multicellular body includes tissue culture medium and a plurality of living cells cohered to one another. The structure includes a plurality of discrete filler bodies. Each filler body includes a biocompatible material that resists migration and ingrowth of cells from the multicellular bodies into the filler bodies. The multicellular bodies are arranged in a pattern in which each multicellular body contacts at least one other multicellular body and the filler bodies are positioned and arranged to form a plurality of acellular channels extending between opposite ends of the structure.

Another aspect of the invention is an axon-guiding graft for restoring nerve function by promoting regenerative axon growth through the graft when the graft is implanted in a living organism having a nervous system and positioned in a gap between the ends of a severed nerve. The graft includes an elongate three-dimensional structure including a plurality of living cells and a plurality of discrete acellular channels extending between opposite ends of the elongate three-dimensional structure.

In another aspect, the invention includes an axon-guiding graft for restoring nerve function by promoting regenerative axon growth through the graft when the graft is implanted in a living organism having a nervous system and positioned in a gap between the ends of a severed nerve. The axon-guiding graft includes an elongate three-dimensional structure made of a plurality of living cells. The living cells include Schwann cells. The elongate three-dimensional structure is an engineered tissue, is not an autologous graft, is non-innervated, and/or includes tissue culture medium.

Still another aspect of the invention is an axon-guiding graft for restoring nerve function by promoting regenerative axon growth through the graft when the graft is implanted in a living organism having a nervous system and positioned in a gap between the ends of a severed nerve. The graft includes an elongate three-dimensional structure comprising a plurality of living cells. The three-dimensional structure includes an outer portion and a central portion extending axially between opposite ends of the outer portion so the outer portion surrounds the central portion. The population of living cells in the central portion includes a higher percentage of Schwann cells than the percentage of Schwann cells in the population of living cells in the outer portion. The elongate three-dimensional structure is an engineered tissue, is not an autologous graft, is non-innervated, and/or includes tissue culture medium.

Still another aspect of the invention is an axon-guiding graft for restoring nerve function by promoting regenerative axon growth through the graft when the graft is implanted in a living organism having a nervous system and positioned in a gap between the ends of a severed nerve. The graft includes an elongate three-dimensional structure comprising a plurality of living cells. The plurality of living cells include Schwann cells. At least one acellular channel extends between opposite ends of the elongate three-dimensional structure. At least one filler body is in the acellular channel. The at least one filler body includes agarose. At least some of the Schwann cells are located along the acellular channel adjacent the filler body.

Another aspect of the invention is a multicellular body including a plurality of living cells cohered to one another. The plurality of living cells includes living cells of a first type and living cells of a second type. The living cells of the first type are Schwann cells and the Schwann cells constitute between about 0.1 percent and about 20 percent of the plurality of living cells.

Still another aspect of the invention is a multicellular body including a plurality of living cells cohered to one another. The plurality of living cells include living cells of a first type and living cells of a second type. The living cells of the first type are bone marrow stem cells and the bone marrow stem cells constitute about 90 percent of the plurality of living cells.

Another aspect of the invention is a three-dimensional structure. The three dimensional structure includes a plurality of elongate multicellular bodies. Each multicellular body includes a plurality of living cells cohered to one another. The bodies have opposite axial ends. The multicellular bodies are arranged in a three-dimensional pattern in which the multicellular bodies have a side-by-side orientation relative to one another and at least one of the ends of one of the multicellular bodies is axially offset from the corresponding end of an adjacent one of the multicellular bodies.

Another aspect of the invention is a method of producing a multicellular construct with multiple axially channels populated with Schwann cells. The method includes the steps of:
1) making multiple types of cell pastes with different concentrations of Schwann cells among the selected living cells,
2) shaping each cell paste into an elongate shape,
3) incubating the shaped cell pastes in a controlled environment to allow the cells to cohere to one another to form elongate multicellular rods,
4) making acellular filler or supporting rods of similar size as the multicellular rods
5) arranging a plurality of multicellular rods and acellular rods according to a pattern such that each of the multicellular rods contacts at least one other multicellular rod, and that the multicellular rods with lower concentrations of Schwann cells are placed in the peripheral layers, while the multicellular rods with higher concentrations of Schwann cells are placed in the center, and
6) allowing the multicellular rods to fuse with at least one other multicellular rod to form the desired construct.

Disclosed herein, in certain embodiments, is a three-dimensional nerve graft construct, comprising: (a) a plurality of first engineered multicellular bodies wherein each engineered multicellular body in the plurality of first engineered multicellular bodies comprises a plurality of first living cells; (b) a plurality of second engineered multicellular bodies wherein each engineered multicellular body in the plurality of second engineered multicellular bodies comprises a plurality of second living cells; and (c) a plurality of discrete filler bodies, wherein each discrete filler body in the plurality of discrete filler bodies comprises a biocompatible material that resists migration and ingrowth of the plurality of first living cells or second living cells; wherein the plurality of discrete filler bodies form a plurality of acellular channels extending longitudinally between a first end and a second end of the three dimensional structure. In some embodiments, the plurality of first living cells and the plurality of second living cells comprises: mesenchymal stem cells, bone marrow stem cells, hair follicle stem cells, olfactory ensheathing cells, fibroblasts, smooth muscle cells, Schwann cells, or any combinations thereof. In some embodiments, the plurality of first living cells comprises Schwann cells. In some embodiments, the plurality of second living cells comprises bone marrow stem cells. In some embodiments, the plurality of first engineered multicellular bodies are concentrated around the plurality of acellular channels. In some embodiments, the plurality of second engineered multicellular bodies are concentrated in the outer periphery of the graft. In some embodiments, the filler bodies comprise agarose.

Disclosed herein, in certain embodiments, is a channeled biological structure, comprising: (a) a plurality of first living cells; (b) a plurality of second living cells; and (c) a plurality of acellular channels; wherein the plurality of acellular channels extends longitudinally between a first end and a second end of the three dimensional structure. In some embodiments, the acellular channels are hollow. In some embodiments, the acellular channels are filled or partially filled with a filler body. In some embodiments, the plurality of first living cells and the plurality of second living cells comprises: mesenchymal stem cells, bone marrow stem cells, hair follicle stem cells, olfactory ensheathing cells, fibroblasts, smooth muscle cells, Schwann cells, or any combinations thereof. In some embodiments, the plurality of first living cells comprises Schwann cells. In some embodiments, the plurality of second living cells comprises bone marrow stem cells. In some embodiments, the plurality of first living cells are concentrated around the plurality of acellular channels. In some embodiments, the plurality of second living cells are concentrated in the outer periphery of the graft.

Disclosed herein, in certain embodiments, is the use of a channeled biological structure disclosed herein for rejoining the proximal and distal stumps of a damaged axon.

Disclosed herein, in certain embodiments, is the use of a channeled biological structure disclosed herein for the manufacture of a nerve graft for rejoining the proximal and distal stumps of a damaged axon.

Other objects and features will in part be apparent and in part pointed out hereinafter.

BRIEF DESCRIPTION OF THE DRAWINGS

FIG. 2B illustrates a sequence in which the three dimensional structure produced in the sequence illustrated in FIG. 2A matures into an axon-guiding graft;

Corresponding reference characters indicate corresponding parts throughout the drawings.

DETAILED DESCRIPTION

Figure 1:
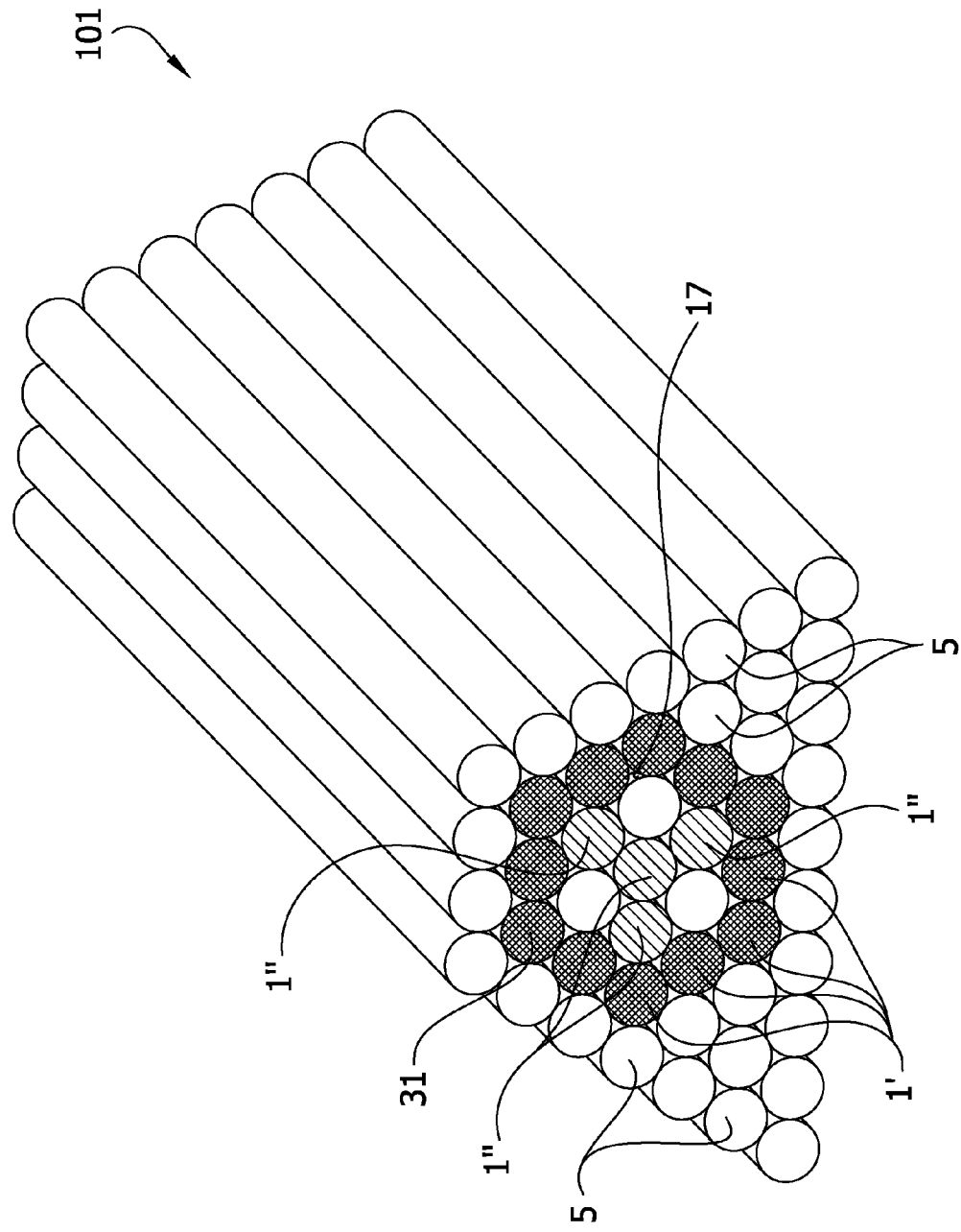
FIG. 1 is a perspective of one embodiment of a three dimensional structure assembled from multicellular bodies and filler bodies.

All publications, patent applications, patents, and other references mentioned herein are incorporated by reference in their entirety.

Annually, over 200,000 peripheral nerve surgeries are performed in the United States alone. Commonly, these procedures require grafts to bridge one or more severed nerves. Spontaneous regeneration of nerves is generally limited to gaps of not more than 3 cm between the two ends. Repair of a ruptured nerve presents a serious clinical challenge because nerves must re-grow, or regenerate, toward their target. In some instances, direct end-to-end reconnection through microsurgery can be used, but use of this technique is limited by the degree to which a nerve can be stretched (generally only about 10% over its original length). The current technology in repairing ruptures with gaps of more than about 3 cm is to use grafts harvested from another location in the patient (i.e., an autologous graft). However, autologous grafts can require multiple surgical procedures and can create further trauma, cause morbidity at the donor site, result in aberrant nerve regeneration due to mismatch between the nerve and the graft, and may ultimately fail to adequately restore nerve function. Moreover, even when the severed nerve in need of repair is a motor nerve, sensory nerves are typically used for autologous grafting, since removal of a sensory nerve from a donor site results in less morbidity than would the removal of a motor nerve (removal of a sensory nerve only results in a loss of sensation, not a loss of motor function). However, the fascicles in motor nerves are significantly larger than the fascicles in sensory nerves. Thus, grafting a sensory nerve into a gap in a motor nerve creates a mismatch in the architecture between the native motor nerve portions and the sensory nerve portion that has been implanted. This mismatch in architecture is thought to be at least partially responsible for the aberrant nerve regeneration which can occur with autologous grafts.

Another approach has been introduced as an alternative for repair of extensive nerve injuries, which relies on guiding the re-growth by entubulating the section ends using natural or artificial conduits. Entubulation techniques can bridge short nerve defects without the morbidities associated with harvesting of autologous nerve grafts, but the outcomes of the repairs differ with different conduit materials. Materials for entubulation may be synthetic or natural (e.g., collagen), or allogenic (i.e., an allograft; e.g., using decellularized human cadaveric nerve).

The use of tissue engineering techniques in the repair of peripheral nerves provides a promising solution for circumventing the problems associated with autologous grafts, allografts, and entubulation techniques. However, despite some scientific advancements, applications of the bioengineered structures for repairing damaged nerves in patients are still very limited. Some studies have shown that a longitudinally-oriented cylindrical structure favors the axonal growth by mimicking endoneural architecture. Other studies have shown that the presence of Schwann cells in certain artificial conduits improves nerve regeneration, but not enough to achieve the level of recovery which is seen with autografts. Moreover, axonal growth can be impaired by inflammatory and immunological responses triggered by the implanted scaffold contained in existing artificial conduit grafts.

Recently, a new tissue engineering technique, "bioprinting," has been developed in the inventors' lab to produce a three-dimensional biological construct having a desired shape. The bioprinting technique is described in U.S. patent application Ser. No. 10/590,446 (published as U.S. Patent Application Publication No. 2008/0070304), and further described in International Patent Application No. PCT/US2009/048530 (published as WO 2010/008905) and corresponding U.S. patent application Ser. No. 12/491,228 (published as U.S. Patent Application Publication No. 2010/0041134). U.S. Patent Application Publication Nos. 2008/0070304 and 2010/0041134 and PCT Publication No. WO 2010/008905 are incorporated by reference herein in their entirety. The bioprinting technique involves the use of engineered multicellular bodies having a plurality of living cells in a method comprising arranging the multicellular bodies in a predetermined pattern and allowing them to fuse to form an engineered tissue. Bioprinting is generally an automated rapid prototyping method allowing for the creation of well-defined architectural features without any scaffold material. The "bioprinting" technique has shown promise for producing three-dimensional tissues.

New structures and methods for producing bioengineered axon-guiding grafts are provided. In particular, a novel engineered biological axon-guiding graft which is capable of serving as a guiding conduit in the nerve regenerative process is provided. The graft is adapted to facilitate axon growth through the guide.

The technology involves the use of multicellular bodies as building blocks that can be used to assemble a three-dimensional construct that can become a desired engineered axon-guiding graft through maturation. Each multicellular body comprises a plurality of living cells that are sufficiently cohered to one another to allow the body to be handled (e.g., picked up and moved) as a single object. The multicellular bodies can be used in conjunction with one or more filler bodies (e.g., bodies comprising a biocompatible material that resists migration and ingrowth of cells from the multicellular bodies into the filler bodies) to assemble constructs that can become, through maturation, an elongate three-dimensional structure having a plurality of acellular channels extending between opposite ends of the structure. The filler bodies can be easily removed from the exterior and, if desired, also from the interior (e.g., from the acellular channels) of a mature engineered tissue. In some cases it can be desirable to implant the graft while one or more filler bodies remain in the graft.

To create the axon-guiding grafts described herein, multicellular bodies and filler bodies are used to form a three-dimensional elongate structure having a plurality of acellular channels extending between opposite ends of the structure. When an axon-guiding graft is implanted at the site of a nerve injury in a human or other animal (e.g., in a gap between the ends of a severed nerve), axons from the proximal native nerve grow through the axon-guiding graft and into the distal end of the nerve structure. Schwann cells, which support nerve development and regeneration, populate at least portions of the interfaces between the acellular channels and the multicellular region in the axon-guiding graft, and this is thought to facilitate the growth of the axons through the graft. Without being bound to any particular theory, neurotrophic factors released by the Schwann cells and/or the transected axons in the damaged nerve may promote growth of axons from the proximal native nerve through the graft and into the distal end of the nerve.

Having provided a general overview of a method of producing a three-dimensional biological engineered tissue using the materials and processes of the present invention, such processes and materials will now be described in more detail.

Multicellular Bodies

Figure 1A:
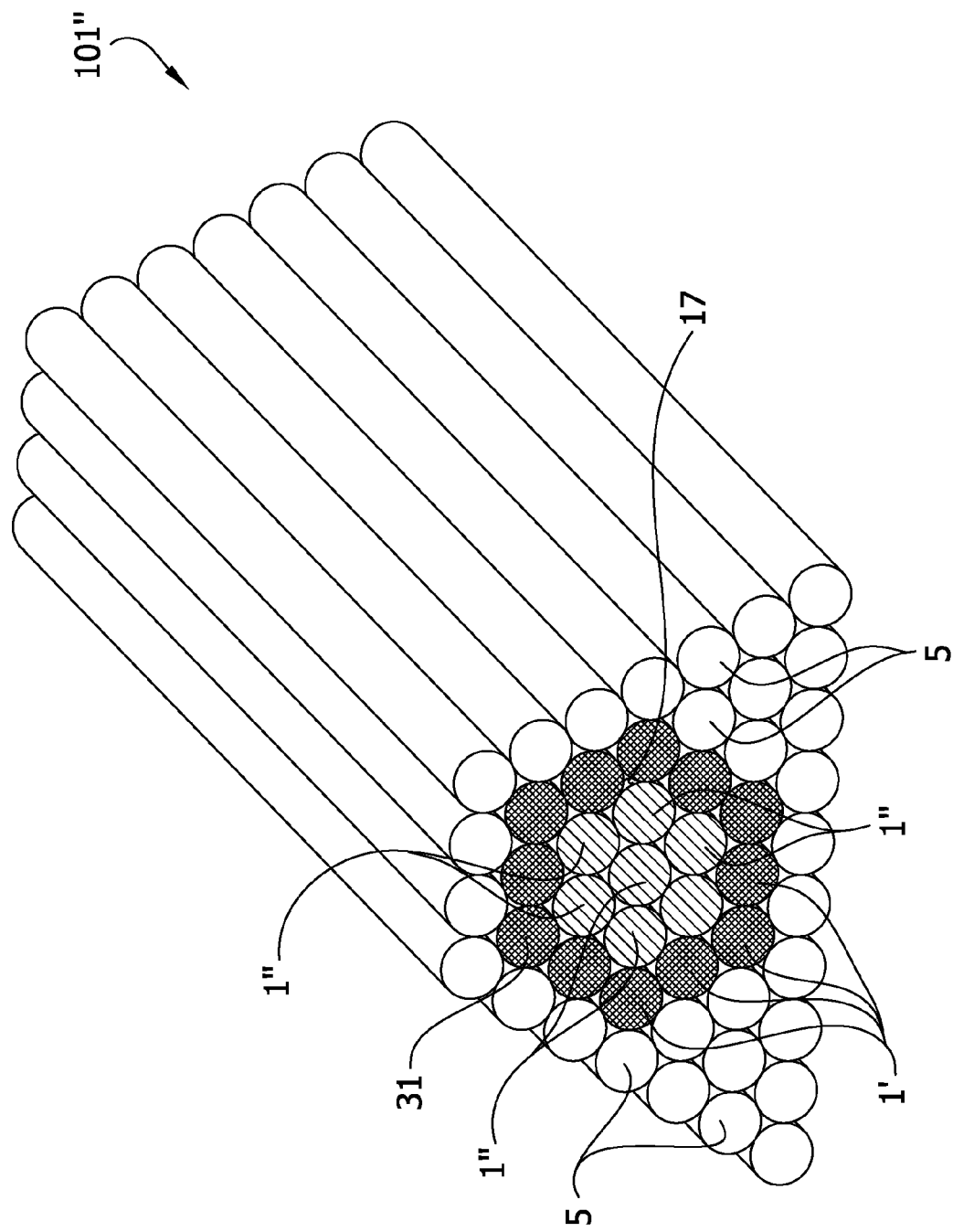
FIG. 1A is a perspective of another embodiment of a three-dimensional structure assembled from multicellular bodies.

The technology involves use of multicellular bodies as building blocks that can be used to assemble a three-dimensional construct (FIGS. 1 and 2) that can become a desired engineered axon-guiding graft through maturation. Multicellular bodies, their use in tissue engineering generally, and their use in making bioengineered blood vessels, are described at length in U.S. patent application Ser. No. 12/491, 228 (published as U.S. Patent Publication No. 2010/0041134), which is incorporated by reference herein in its entirety. In particular, the multicellular bodies are described throughout U.S. Patent Publication No. 2010/0041134, for example at paragraphs [0054], [0055], and [0057]-[0072], and are illustrated in FIGS. 1A-1C of U.S. Patent Publication No. 2010/0041134.

Briefly, each multicellular body comprises a plurality of living cells that are sufficiently cohered to one another to allow the body to be handled (e.g., picked up and moved) as a single object. The cohesion of the multicellular body is suitably sufficient to allow the body to support itself (e.g., on a work surface or in an assembly that includes multiple multicellular bodies) for a period of time sufficient to enable the living cells to cohere to the living cells of an adjoining multicellular body. The ability to pick up and move a plurality of living cells in the form of a self-supporting multicellular body provides flexibility to assemble numerous different three-dimensional constructs. For example, the multicellular bodies can be used in conjunction with one or more filler bodies (e.g., bodies comprising a biocompatible material that resists migration and ingrowth of cells from the multicellular bodies into the filler bodies and which may also resist adherence of cells to the filler bodies) to assemble constructs that can become, through maturation, an elongate three-dimensional structure having a plurality of acellular channels extending between opposite ends of the structure. The multicellular bodies and filler bodies can also be used to assemble constructs that become engineered tissues having other shapes through maturation. Further, because the multicellular bodies are self-supporting, there is no need to embed the multicellular bodies in a supporting gel or scaffold. Instead, the ability to "print in air" or in a low-viscosity tissue culture medium facilitates arranging the multicellular bodies in a manner that ensures the multicellular bodies are in direct contact with one another. Better contact between the multicellular bodies can facilitate efficient and reliable fusion of the multicellular bodies during maturation. In addition, the filler bodies can be easily removed from the exterior and, if desired, also from the interior (e.g., the lumen or acellular channels of a tubular structure) of a mature engineered tissue.

In addition, the methods described herein use elongate (e.g., substantially rod-shaped or rod-shaped) multicellular bodies as the building blocks for the engineered axon-guiding grafts. Because elongate multicellular bodies are already cohered to one another over a significant length along a longitudinal axis of the body, fusion of the multicellular bodies is more reliable and can be achieved in less time. Further, elongate multicellular bodies can be arranged in side-by-side adjoining relation to establish contact between the multicellular bodies along a contact area having a substantial length. This can facilitate rapid and reliable fusion of the adjoining multicellular bodies to one another. Although the multicellular bodies illustrated in the drawings of this application are cylindrical rods, it is understood the shape of the multicellular bodies can vary within the broad scope of the invention.

Each multicellular body comprises a plurality of living cells cohered to one another so the cells together form a desired three-dimensional (3-D) shape with viscoelastic consistency and sufficient integrity for easy manipulation and handling during a bio-engineering process, such as tissue or organ engineering. Sufficient integrity means that the multicellular body, during the subsequent handling, is capable of retaining its physical shape, which is not rigid, but has a viscoelastic consistency, and maintaining the vitality of the cells.

The multicellular bodies may be composed of one or more pre-selected cell types. The cells used to form the multicellular bodies which are used to construct the axon-guiding grafts can advantageously comprise a cell type or cell types typically found in nervous system tissues (e.g., glial cells such as Schwann cells with or without satellite glial cells additionally being present). The cells used to form the multicellular bodies can also advantageously comprise a cell type or cell types which exhibit one or more anti-inflammatory properties (e.g., bone marrow stem cells (BMSCs) or mesenchymal stem cells). The inclusion of cells exhibiting anti-inflammatory properties in the multicellular bodies can mitigate the inflammation which has been observed at the site of implantation with other types of nerve grafts. Inflammation can promote scar tissue formation and may impede ingrowth of axons into the graft, and thus is undesirable for optimal restoration of nerve function. Other cell types which can suitably be used to form the multicellular bodies include, but are not limited to hair follicle stem cells, olfactory ensheathing cells, fibroblasts, and smooth muscle cells.

The multicellular bodies may be homocellular or heterocellular. In homocellular multicellular bodies, the plurality of living cells includes a plurality of living cells of a single cell type. Almost all of the living cells in a homocellular multicellular body are cells of the single cell type, subject to some tolerance for low levels of impurities including a relatively small number of cells of a different cell type that have no more than a negligible impact on the maturation of a construct including the homocellular multicellular body. In contrast, a heterocellular multicellular body includes significant numbers of cells of more than one cell type. For example, a multicellular body can comprise a plurality of living cells of a first type and a plurality of living cells of a second type (etc.), the second cell type being different from the first cell type. Heterocellular multicellular bodies can also include a plurality of cells of a first cell type, a plurality of cells of a second cell type, and a plurality of cells of a third cell type with each of the first, second and third cell types being different from the others of the first, second, and third cells types.

The living cells in a heterocellular body may remain unsorted or can "sort out" (e.g., self-assemble) during the fusion process to form a particular internal structure for the engineered tissue. The sorting of cells is consistent with the predictions of the Differential Adhesion Hypothesis (DAH). The DAH explains the liquid-like behavior of cell populations in terms of tissue surface and interfacial tensions generated by adhesive and cohesive interactions between the component cells. In general, cells can sort based on differences in the adhesive strengths of the cells. For example, cell types that sort to the interior of a heterocellular multicellular body generally have a stronger adhesion strength (and thus higher surface tension) than cells that sort to the outside of the multicellular body.

For creating the axon-guiding grafts, in some embodiments, a combination of homocellular and heterocellular multicellular bodies can be used. For example, heterocellular multicellular bodies wherein the cells of the first type are Schwann cells and the cells of the second type are BMSCs (or another cell type having anti-inflammatory properties) can be used together with homocellular multicellular bodies wherein the plurality of living cells are BMSCs (or another cell type having anti-inflammatory properties) to create an axon-guiding graft. In the heterocellular multicellular bodies wherein the cells of the first type are Schwann cells and the cells of the second type are BMSCs (or another cell type having anti-inflammatory properties), the Schwann cells suitably constitute between about 0.1 percent to about 20 percent (v/v) of the plurality of living cells in the multicellular body, more suitably between about 1 percent to about 15 percent (v/v) of the plurality of living cells in the multicellular body, and still more suitably between about 3 percent to about 10 percent (v/v) of the plurality of living cells in the multicellular body, and even still more suitably between about 5 percent and about 10 percent (v/v) of the plurality of living cells in the multicellular body. For example, the Schwann cells suitably constitute about 10% (v/v) of the plurality of living cells in the multicellular body. The remainder of the plurality of living cells in the multicellular body can be BMSCs, BMSCs in combination with one or more other cell types, or any other suitable cell type.

As an additional example, the axon-guiding grafts can be constructed using a first type of heterocellular multicellular body which has a relatively higher percentage of Schwann cells, and a second type of heterocellular multicellular body which has a relatively lower percentage of Schwann cells. In such a case, in the heterocellular multicellular bodies having a relatively higher percentage of Schwann cells, the Schwann cells suitably constitute between about 0.1 percent to about 20 percent (v/v) of the plurality of living cells in the multicellular body, more suitably constitute between about 1 percent to about 15 percent (v/v) of the plurality of living cells in the multicellular body, and still more suitably constitute between about 3 percent to about 10 percent (v/v) of the plurality of living cells in the multicellular body, and even still more suitably between about 5 percent and about 10 percent (v/v) of the plurality of living cells in the multicellular body. For example, the Schwann cells suitably constitute about 10% (v/v) of the plurality of living cells in the multicellular bodies having a relatively higher percentage of Schwann cells. The heterocellular multicellular bodies having a relatively lower percentage of Schwann cells can be substantially devoid of Schwann cells or can comprise a percentage of Schwann cells which is lower than the percentage of Schwann cells in the heterocellular multicellular bodies having a relatively higher percentage of Schwann cells.

The cells used to make the multicellular bodies can be cells from a non-autologous source or cells from an autologous source. When cells from an autologous source are used, the cells can be harvested from the individual having the nerve injury to be repaired, expanded in tissue culture, and used to make the multicellular bodies. For example, in embodiments where the multicellular bodies comprise Schwann cells and/or bone marrow stem cells, these cells can be harvested from a human or other animal having a nerve injury in need of repair and can be used to make the multicellular bodies. For instance, the Schwann cells can be harvested by biopsy during resection of the damaged nerve or another surgical procedure. Alternatively, olfactory ensheathing cells or hair follicle stem cells could be harvested from the human or animal having a nerve injury in need of repair and differentiated into Schwann cells. BMSCs can be harvested from the patient's bone marrow using various procedures known in the art, for example by bone marrow aspiration or bone marrow biopsy (e.g., using a bone marrow biopsy gun). The harvested Schwann cells and BMSCs can then be expanded in tissue culture in order to generate a sufficient number of cells for making the multicellular bodies.

In some instances, the multicellular body suitably includes one or more extracellular matrix (ECM) components or one or more derivatives of one or more ECM components in addition to the plurality of cells. For example, the multicellular bodies may contain various ECM proteins (e.g., gelatin, fibrinogen, fibrin, collagen, fibronectin, laminin, elastin, and/or proteoglycans). The ECM components or derivatives of ECM components can be added to a cell paste used to form the multicellular body, as discussed in further detail below. The ECM components or derivatives of ECM components added to the cell paste can be purified from a human or animal source, or produced by recombinant methods known in the art. Alternatively, the ECM components or derivatives of ECM components can be naturally secreted by the cells in the multicellular body, or the cells used to make the multicellular body can be genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and cadherins). The ECM components or derivatives of ECM components may promote cohesion of the cells in the multicellular body. For example, gelatin and/or fibrinogen can suitably be added to the cell paste which is used to form the multicellular body. The fibrinogen can then be converted to fibrin by the addition of thrombin.

The multicellular body in some instances suitably includes a tissue culture medium. The tissue culture medium can be any physiologically compatible medium and will typically be chosen according to the cell type(s) involved as is well known in the art. The tissue culture medium may comprise, for example, basic nutrients such as sugars and amino acids, growth factors, antibiotics (to minimize contamination), etc.

Furthermore, the multicellular body can suitably be non-innervated (i.e., it is substantially free of neurons) or non-cartilaginous, or both non-innervated and noncartilaginous. The multicellular body can be described as an "engineered" multicellular body because it is different from biological structures that arise without the guidance of human ingenuity. In other words, the multicellular body is synthetic, or non-naturally occurring.

The multicellular body can have various sizes and shapes within the scope of the invention. For example, the multicellular body can suitably have an elongate shape, and more suitably can be substantially cylindrically shaped (e.g., substantially rod-shaped). The multicellular bodies generally have the same dimensions and characteristics as described in U.S. Patent Publication No. 2010/0041134 at paragraphs [0067]-[0072]. The length of the multicellular bodies used to make the axon guiding grafts is suitably at least about 1 centimeter, more suitably at least about 2 centimeters, and still more suitably at least about 3 centimeters. The length of the multicellular bodies used to make the axon guiding grafts is suitably less than about 7 centimeters, more suitably less than about 6 centimeters, and still more suitably less than about 5 centimeters. Thus, for example, the multicellular bodies suitably have a length in the range of about 1 centimeter to about 7 centimeters, more suitably in the range of about 2 centimeters to about 6 centimeters, and still more suitably in the range of about 3 centimeters to about 5 centimeters.

Figure 2:
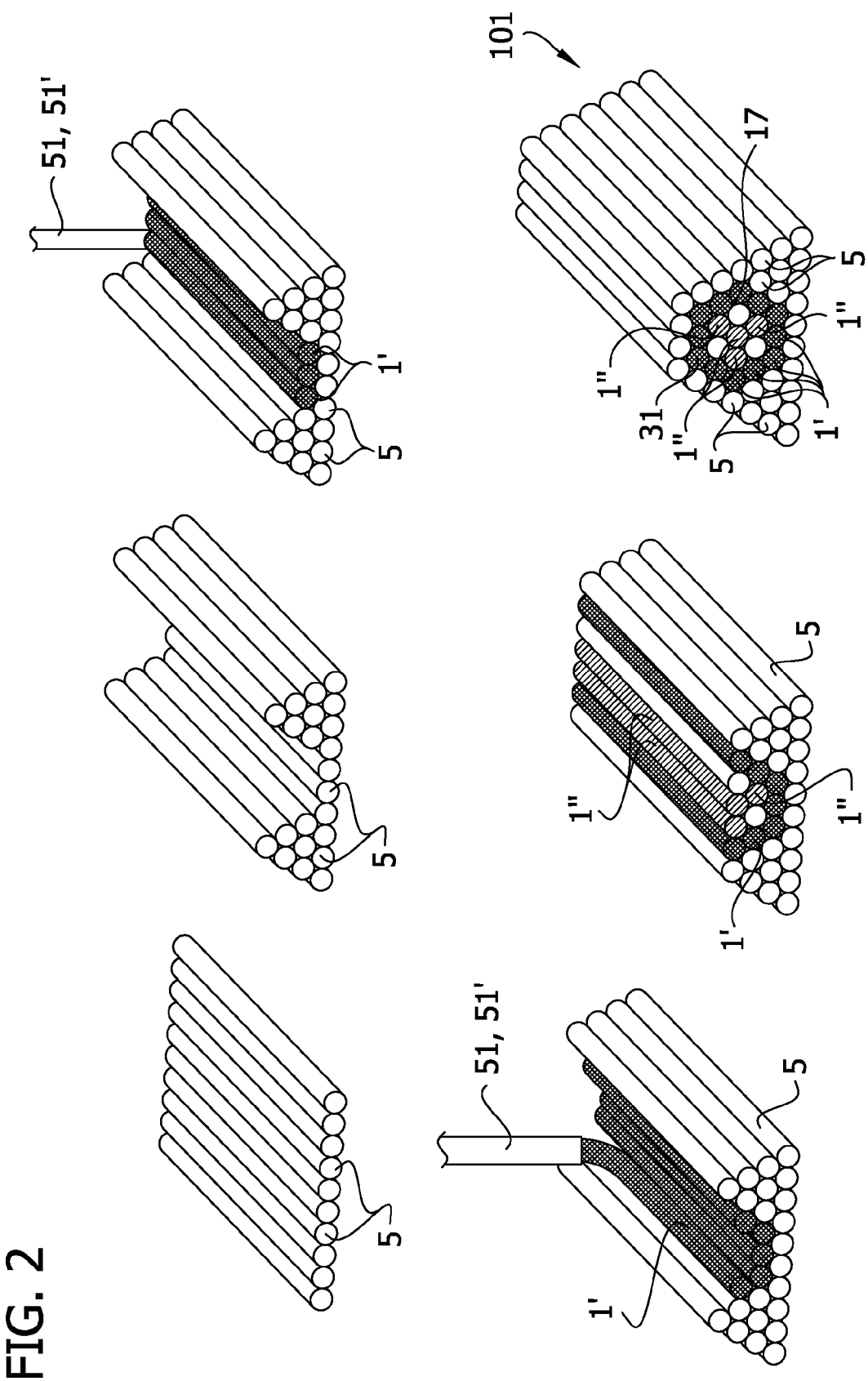
FIG. 2 illustrates one embodiment of a sequence in which multiple multicellular bodies and filler bodies are stacked on top of one another according to a predetermined pattern to form the three-dimensional structure illustrated in FIG. 1.

Although the multicellular bodies 1 illustrated in FIGS. 1 and 2 are substantially cylindrical and have substantially circular cross sections, multicellular bodies having different sizes and shapes are within the scope of the invention. For example, the multicellular body can be an elongate shape (e.g., a cylindrical shape) with a square, rectangular, triangular, or other non-circular cross sectional shape within the scope of the invention. Likewise, the multicellular body can have a generally spherical shape, a non-elongate cylindrical shape, or a cuboidal shape within the scope of the invention.

Method of Making the Multicellular Bodies

Methods of making multicellular bodies are described in U.S. Patent Application Publication No. 2010/0041134 at paragraphs [0073]-[0096], and illustrated in FIGS. 3A-3D, 4A-4D, 5A-5C, and 6A-6C of that publication. The multicellular bodies which are used to construct the axon-guiding grafts described herein are generally prepared in the same manner.

Briefly, there are various ways to make multicellular bodies having the characteristics described above within the scope of the invention. For example, a multicellular body can be fabricated from a cell paste containing a plurality of living cells or with a desired cell density and viscosity. The cell paste can be shaped into a desired shape and a multicellular body formed through maturation (e.g., incubation). In another example, an elongate multicellular body is produced by shaping a cell paste including a plurality of living cells into an elongate shape. The cell paste is incubated in a controlled environment to allow the cells to cohere to one another to form the elongate multicellular body. In yet another example, a multicellular body is produced by shaping a cell paste including a plurality of living cells in a device that holds the cell paste in a three-dimensional shape. The cell paste is incubated in a controlled environment while it is held in the three dimensional shape for a sufficient time to produce a body that has sufficient cohesion to support itself on a flat surface, as described above.

The cell paste can suitably be provided by: (A) mixing cells or cell aggregates (the cells or cell aggregates may include a single cell type or two or more different cell types) and a cell culture medium (e.g., in a pre-determined ratio) to result in a cell suspension, and (B) compacting the cellular mixture to produce the cell paste with a desired cell density and viscosity. The compacting may be achieved by a number of methods, such as by concentrating a particular cell suspension that resulted from cell culture to achieve the desired cell concentration (density), viscosity, and consistency required for the cell paste. For example, a relatively dilute cell suspension from cell culture may be centrifuged for a determined time to achieve a cell concentration in the pellet that allows shaping in a mold. Tangential flow filtration ("TFF") is another suitable method of concentrating or compacting the cells. Compounds may also be combined with the cell suspension to lend the extrusion properties required. Some examples of suitable compounds that may be used in the present invention include collagen, hydrogels, Matrigel, nanofibers, self-assembling nanofibers, gelatin, fibrinogen, etc.

Thus, the cell paste used in these methods is suitably produced by mixing a plurality of living cells with a tissue culture medium, and compacting the living cells (e.g., by centrifugation). If one or more ECM components, or one or more derivatives of one or more ECM components are to be included in the cell paste (as discussed in further detail below), the cell pellet can suitably be resuspended in one or more physiologically acceptable buffers containing the ECM component(s) or derivative(s) of ECM.

The cell density of the cell paste desired for further processing may vary with cell types. The interactions between cells determine the properties of the cell paste, and different cell types will have a different relationship between cell density and cell-cell interaction. The cells may be pre-treated to increase cellular interactions before shaping the cell paste. For example, cells may be incubated inside a centrifuge tube after centrifugation in order to enhance cell-cell interactions prior to shaping the cell paste Various methods may be used to shape the cell paste under the present invention. For example the cell paste can be manipulated, manually molded or pressed (e.g., after concentration/compaction) to achieve the desired shape. For example, the cell paste may be taken up (e.g., aspirated) into a preformed instrument, such as a micropipette (e.g., a capillary pipette), that shapes the cell paste to conform to an interior surface of the instrument. The cross sectional shape of the micropipette (e.g., capillary pipette) can be circular, square, rectangular, triangular, or other non-circular cross sectional shape. The cell paste may also be shaped by depositing it into a preformed mold, such as a plastic mold, metal mold, or a gel mold. Furthermore, centrifugal casting or continuous casting may be used to shape the cell paste.

Figure 3A:
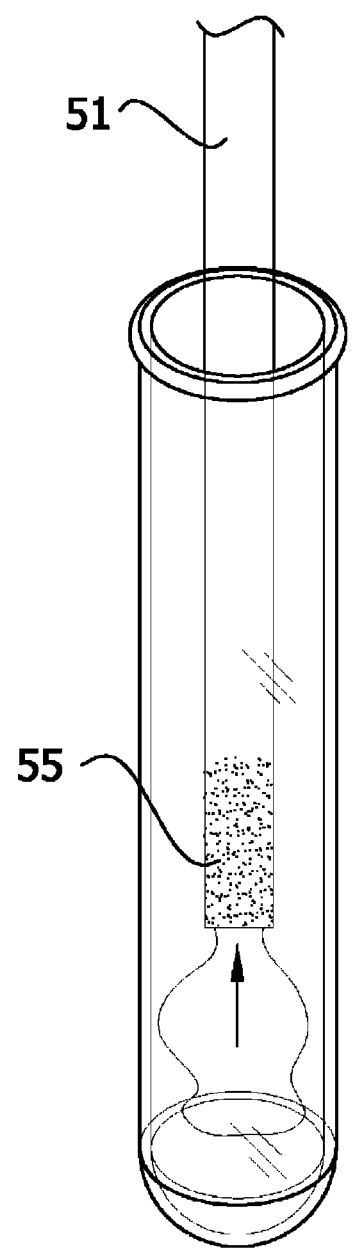
FIG. 3A-3D illustrate one embodiment of a method of making multicellular bodies.
Figure 3B:
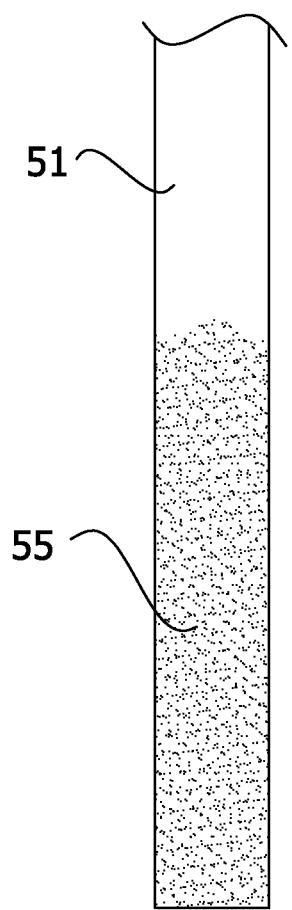

In one example of the method, the shaping includes retaining the cell paste in a shaping device to allow the cells to partially cohere to one another in the shaping device. For example, as illustrated in FIG. 3A, cell paste 55 can be aspirated into a shaping device 51 (e.g., a capillary pipette) and held in the shaping device for a maturation period (also referred to herein as an incubation period) (FIG. 3B) to allow the cells to at least partially cohere to one another. If the cells are able to achieve sufficient cohesion in the first shaping device 51, the multicellular body 1 can be produced in a process that has only a single maturation step (e.g, a single incubation step). For example, the method suitably includes shaping the cell paste 55 in a single shaping device 51 and incubating the shaped cell paste in a single controlled environment to allow the cells to cohere to one another to form the multicellular body. If this is the case, the shaping device 51 (e.g., capillary pipette) can suitably be part of a printing head of a bioprinter or similar apparatus operable to automatically place the multicellular body in a three-dimensional construct, as will be described in more detail below. The inclusion of ECM components or derivatives of ECM components, for example gelatin and/or fibrinogen, in the cell paste may facilitate production of a multicellular body in a single maturation step because such components can promote the overall cohesivity of the multicellular body. However, there is a limit to the amount of time cells can remain in a shaping device such as a capillary pipette, which provides the cells only limited access at best to oxygen and/or nutrients, before viability of the cells is impacted.

Figure 4A:
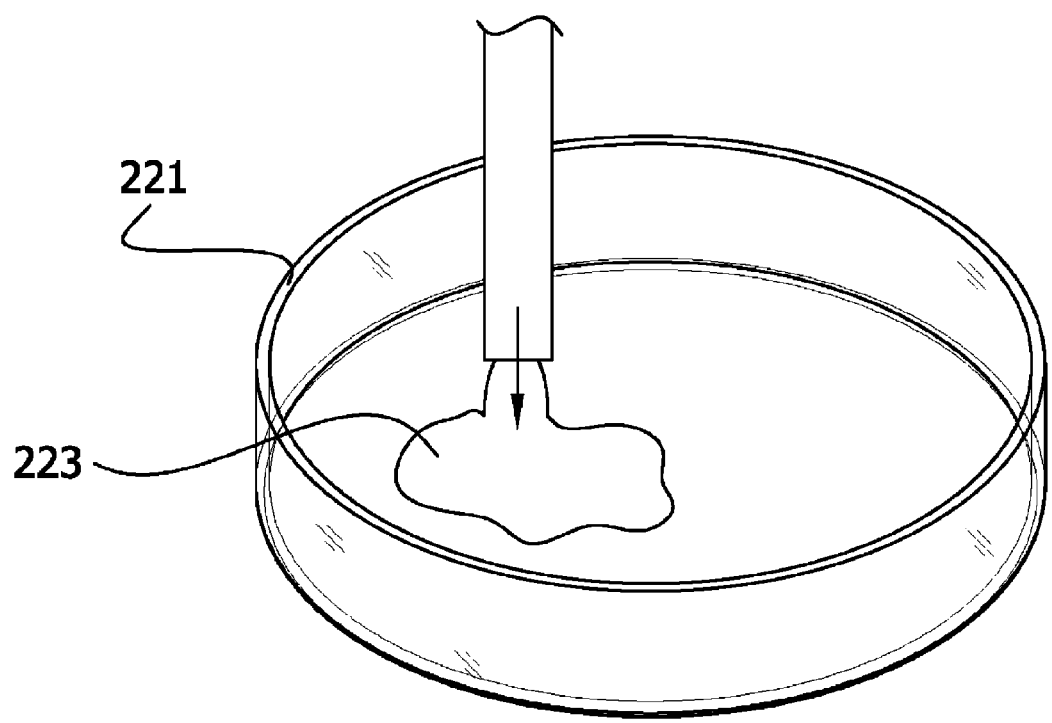
FIGS. 4A-4C illustrate one embodiment of a method of making a mold suitable for use in making muticellular bodies.
Figure 4B:
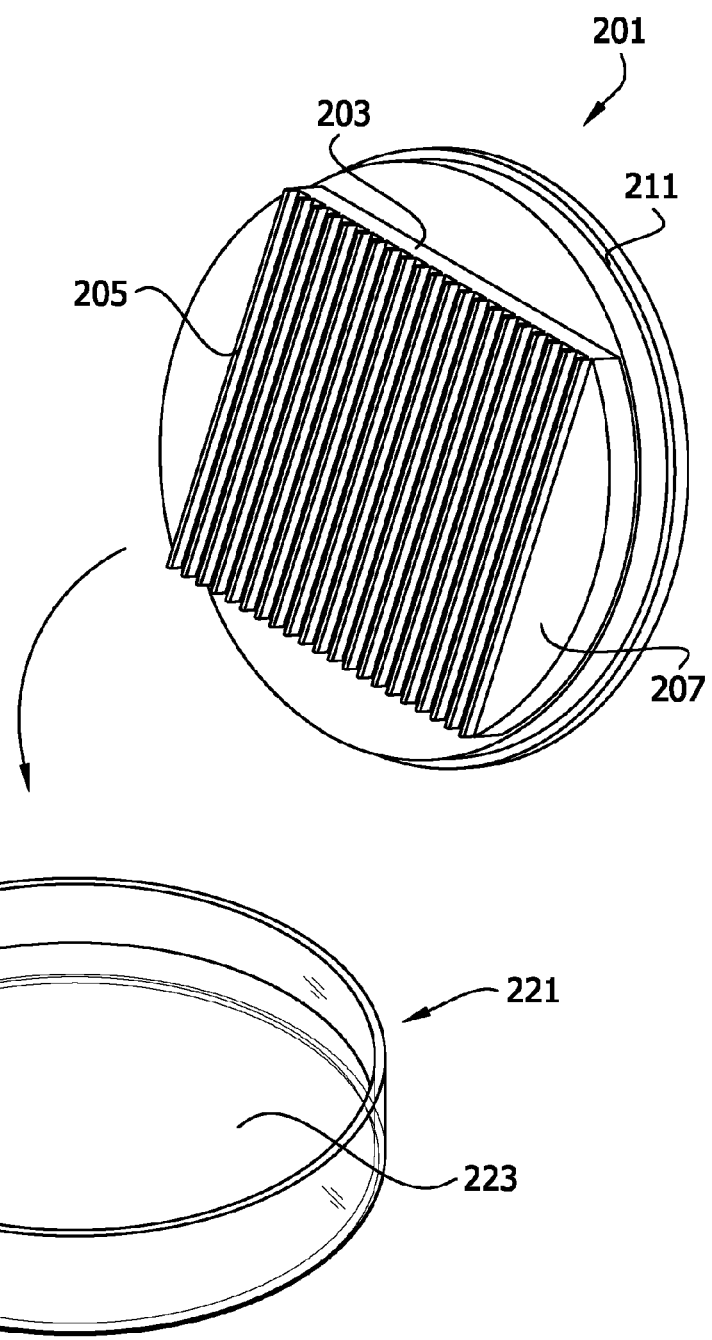
Figure 4C:
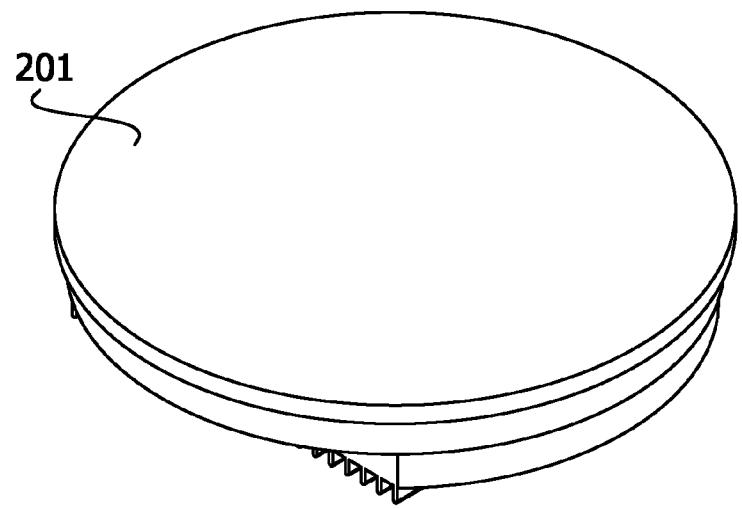
Figure 4C:
Figure 4C:
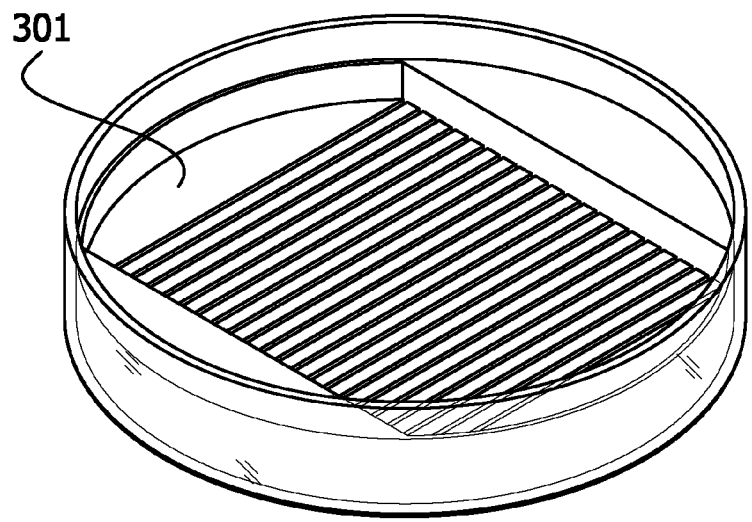

If the cells cannot be retained in the shaping device 51 for a maturation period long enough to achieve the desired cohesion, the partially cohered cell paste 55 is suitably transferred from the shaping device (e.g., capillary pipette) to a second shaping device 301 (e.g., a mold) that allows nutrients and/or oxygen to be supplied to the cells while they are retained in the second shaping device for an additional maturation period. One example of a suitable shaping device 301 that allows the cells to be supplied with nutrients and oxygen and a method of making the mold is illustrated in FIGS. 4A-4C. This shaping device is a mold 301 for producing a plurality of multicellular bodies (e.g., substantially identical multicellular bodies). The mold 301 includes a biocompatible substrate 303 made of a material that is resistant to migration and ingrowth of cells into the substrate and resistant to adherence of cells to the substrate. The mold 301 may be made of any material that will exclude the cells from growing or migrating into or adhering to the mold. For example, the substrate 303 can suitably be made of Teflon® (PTFE), stainless steel, hyaluronic acid, agarose, agar, polyethylene glycol, glass, metal, plastic, or gel materials (e.g., agarose gel or other hydrogel), and similar materials.

Figure 3C:
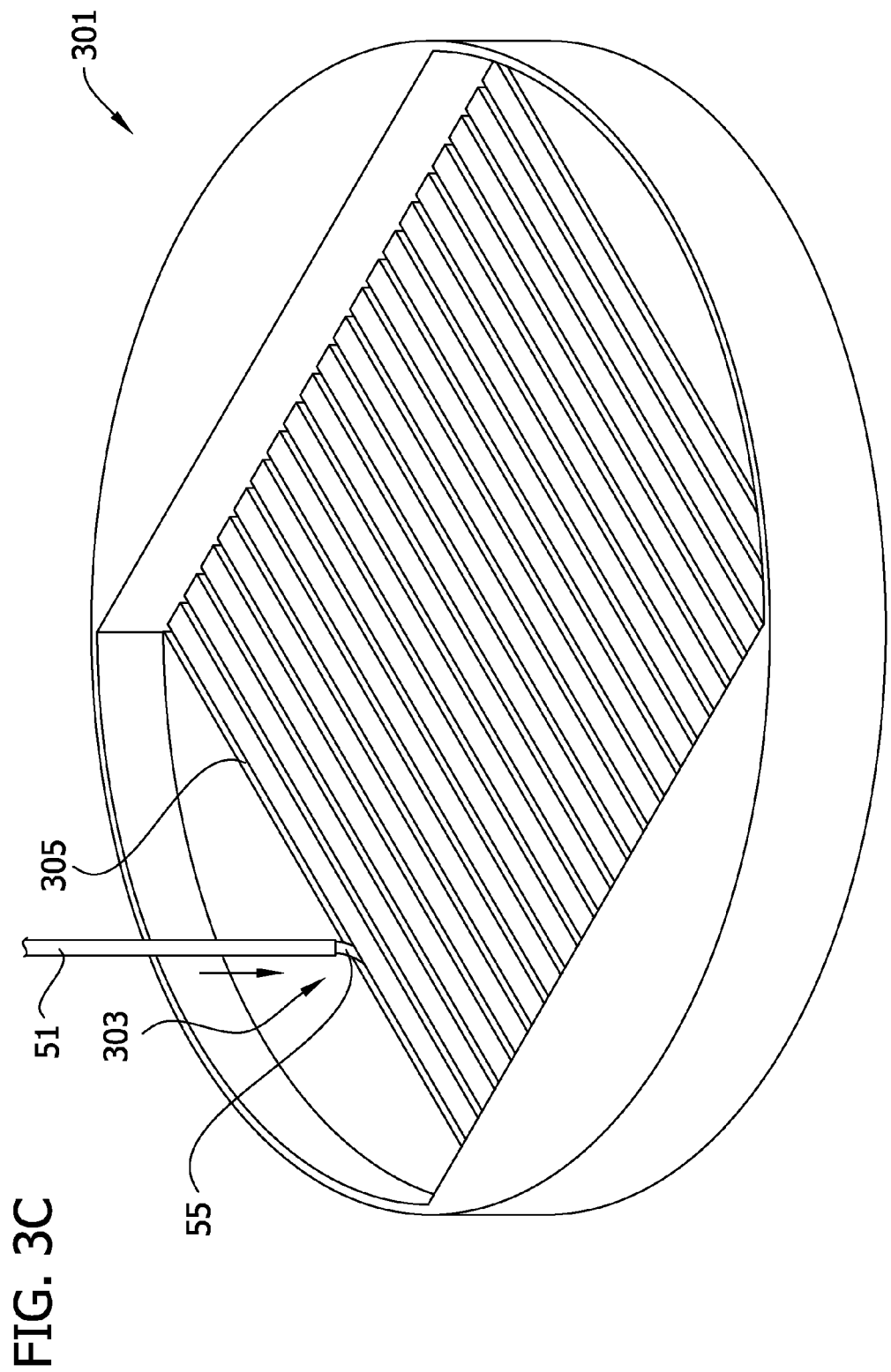
Figure 3D:
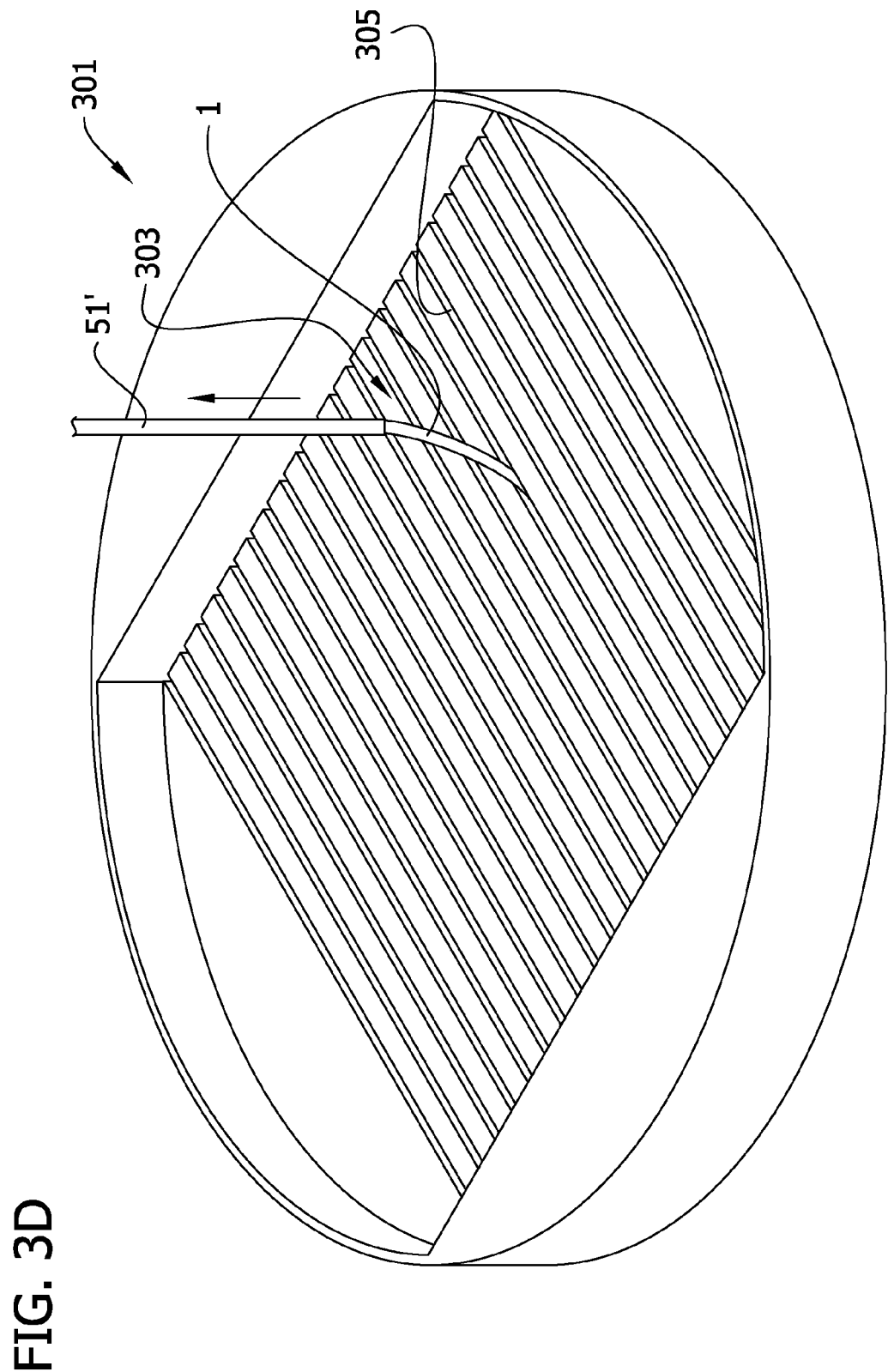

The substrate 303 is shaped to receive a composition comprising plurality of cells having a relatively lower cohesion (e.g., from the first shaping device 51) and hold the composition in a desired three-dimensional shape during a maturation period during which the cohesion of the cells increases to form a multicellular body that has a greater cohesion relative to the composition before the maturation period, such as a multicellular body having any of the characteristics of the multicellular body described above. The mold 301 is also suitably configured so tissue culture media can be supplied to the cell paste 55 (e.g., by dispensing tissue culture media onto the top of the mold). For example, as illustrated in FIGS. 3C and 3D, a plurality of elongate grooves 305 are formed in the substrate 303. The elongate grooves 305 of the mold 301 generally have the same dimensions and characteristics as described in U.S. Patent Application Publication No. 2010/0041134 at paragraph [0080].

There are various ways to make a suitable mold within the scope of the invention. For example, FIGS. 4A-4C illustrate one embodiment of a tool, generally designated 201, that can be used to make a mold that is suitable for making the multicellular bodies described above. In general, a portion of the tool 201 is configured to be a negative of the portion of the mold 301 that retains the partially cohered cell paste during the second maturation period. For example, the tool 201 suitably includes a body 203 and a plurality of projections 205 extending from the body. Each projection 205 is suitably sized and shaped to form a depression or receiving area in the mold substrate that will retain cell paste 55 in a shape such that none of the cells in the depression/receiving area formed in the mold by the projection is more than about 300 microns from an exterior surface of the shaped cell paste. Further details regarding this embodiment of the tool are provided in paragraph [0082] and FIGS. 5A-5C of U.S. Patent Application Publication No. 2010/0041134.

To make the mold 301 a cell culture dish 221 is suitably filled with a liquid 223 that can be made to solidify or set up as a gel, as illustrated in FIG. 4A. For example, the liquid can be an agarose solution 223. The tool 201 is placed on top of the cell culture dish 221 FIG. 4B so the lip 211 sits on the rim 225 of the cell culture dish and the projections 205 (e.g., fins) extend from the bottom 207 of the tool 201 into the liquid 223. The liquid 223 is allowed to set up to form a solid or gel substrate surrounding the distal ends of the projections 205 (e.g., fins). Then tool 201 is lifted off the cell culture dish to separate the tool 201 from the newly produced mold 301 FIG. 4C.

Thus, if a second shaping device is used, the partially cohered cell paste 55 is suitably transferred from the first shaping device 51 (e.g., a capillary pipette) to the second shaping device (e.g., the mold 301 illustrated in FIG. 4C. The partially cohered cell paste 55 can be transferred by the first shaping device 51 (e.g., the capillary pipette) into the grooves 305 of the mold 301. Thus, the method includes transferring the partially cohered cell paste 55 to a second shaping device 301, and retaining the partially cohered cell paste in the second shaping device to form the multicellular body. Following a maturation period in which the mold 301 is incubated along with the cell paste 55 retained therein in a controlled environment to allow the cells in the cell paste to further cohere to one another to form the multicellular body 1, the cohesion of the cells will be sufficiently strong to allow the resulting multicellular body 1 to be picked up with a capillary pipette or other instrument. The capillary pipette 51 (now containing the mature multicellular body 1 that has been picked up out of a groove 305 in the mold 301) can suitably be part of a printing head of a bioprinter or similar apparatus operable to automatically place the multicellular body into a three-dimensional construct, as will be described in more detail below.

Thus, in one example of the method of making a multicellular body 1, the shaping includes retaining the cell paste 55 in a first shaping device 51 to allow the cells to partially cohere to one another in the first shaping device, transferring the partially cohered cell paste to a second shaping device 301, and retaining the partially cohered cell paste in the second shaping device to form the multicellular body 1. However, in some embodiments, such as when gelatin and/or fibrinogen are added to the cell paste, the cells may sufficiently cohere to form the multicellular body in the first shaping device 51, and the step of transferring the cell paste 55 to a second shaping device 301 and retaining the cell paste in the second shaping device may be unnecessary.

The first shaping device 51 can suitably include a capillary pipette and the second shaping device can include a device that allows nutrients and oxygen to be supplied to the cells while they are retained in the second shaping device, such as the above-described mold 301.

The cross-sectional shape and size of the multicellular bodies will substantially correspond to the cross-sectional shapes and sizes of the first shaping device and optionally the second shaping device used to make the multicellular bodies, and the skilled artisan will be able to select suitable shaping devices having suitable cross-sectional shapes, cross-sectional areas, diameters, and lengths suitable for creating multicellular bodies having the cross-sectional shapes, cross-sectional areas, diameters, and lengths discussed above.

As discussed above, a large variety of cell types may be used to create the multicellular bodies of the present invention. Thus, one or more types of cells or cell aggregates, both human and animal somatic cells, including, for example, all of the cell types listed above, may be employed as the starting materials to create the cell paste. For instance, cells such as Schwann cells, BMSCs, mesenchymal stem cells, hair follicle stem cells, olfactory ensheathing cells, fibroblasts, and smooth muscle cells, may be employed. A sample of autologous cells from an intended recipient of an axon-guiding graft (obtained, for example, by biopsy, as described above), can be cultured to produce a sufficient quantity of cells for fabrication of the multicellular bodies. Alternatively, a sample of cells from a non-autologous donor or cells from one or more established cell lines can be cultured to produce a sufficient quantity of cells for fabrication of the multicellular bodies. Multicellular bodies made from autologous cells from an intended recipient are advantageous for avoiding host inflammatory responses or other acute or chronic rejection of the transplanted tissue by the recipient.

As noted above, the multicellular body can be homocellular or heterocellular. For making homocellular multicellular bodies, the cell paste suitably is homocellular. Almost all of the living cells in cell paste to be used for creating a homocellular multicellular body will be cells of a single cell type (e.g., bone marrow stem cells), subject to some tolerance for low levels of impurities, including a relatively small number of cells of a different cell type that have no more than a negligible impact on the maturation of a construct which includes homocellular multicellular bodies made from such cell paste. For making homocellular multicellular bodies which are in turn to be used to make axon guiding grafts, the plurality of living cells in the cell paste can suitably be BMSCs.

For making heterocellular multicellular bodies, on the other hand, the cell paste will suitably include significant numbers of cells of more than one cell type (i.e., the cell paste will be heterocellular). For example, the cell paste can comprise a plurality of living cells of a first type and a plurality of living cells of a second type, the second cell type being different from the first cell type. In another example, the cell paste can comprise a plurality of living cells of a first cell type, a plurality of living cells of a second cell type, and a plurality of living cells of a third cell type. Thus, if the cell paste is to be used to make heterocellular multicellular bodies which in turn are to be used to make axon-guiding grafts, the plurality of living cells in the cell paste can suitably include two or more cell types selected from Schwann cells, BMSCs, mesenchymal stem cells, hair follicle stem cells, olfactory ensheathing cells, fibroblasts, and smooth muscle cells. For example, the plurality of living cells may include BMSCs and Schwann cells. Such heterocellular multicellular bodies can suitably be used in combination with homocellular multicellular bodies composed of BMSCs to construct the axon guiding grafts, as will be described in greater detail below. As described in greater detail above, when heterocellular cell paste is used to create the multicellular bodies, the living cells may "sort out" during the maturation and cohesion process based on differences in the adhesive strengths of the cells, and may recover their physiological conformation.

In addition to the plurality of living cells, one or more ECM components or one or more derivatives of one or more ECM components (e.g., gelatin, fibrinogen, collagen, fibronectin, laminin, elastin, and/or proteoglycans) can suitably be included in the cell paste to incorporate these substances into the multicellular bodies, as noted above. The ECM components or derivatives of ECM components added to the cell paste can be purified from a human or animal source, or produced by recombinant methods known in the art. Adding ECM components or derivatives of ECM components to the cell paste may promote cohesion of the cells in the multicellular body. For example, gelatin and/or fibrinogen can be added to the cell paste. More particularly, a solution of 10-30% gelatin and a solution of 10-80 mg/ml fibrinogen can be mixed with a plurality of living cells to form a cell suspension containing gelatin and fibrinogen. The cell suspension can then be compacted (e.g., by centrifugation) to form the cell paste. The cell paste formed by this process can then be shaped and incubated in a controlled environment to allow the cells to cohere to one another to form the multicellular body. The fibrinogen can be converted to fibrin by the addition of thrombin (e.g., during the printing process). When ECM components or derivatives of ECM components such as, for example, gelatin and fibrinogen, are included in the cell paste, the shaping step suitably comprises retaining the cell paste in a single shaping device to form the multicellular body, and the incubating step suitably comprises incubating the shaped cell paste in a single controlled environment to allow the cells to cohere to one another to form the multicellular body.

The present invention also provides a method for fabrication of a multicellular body comprising a plurality of cells or cell aggregates formed in a desired three-dimensional shape. The inventive fabrication method generally comprises the steps of 1) providing a cell paste containing a plurality of pre-selected cells or cell aggregates (e.g., with a desired cell density and viscosity), 2) shaping the cell paste (e.g., into a desired shape), and 3) forming the multicellular body through maturation.

The aforesaid forming step may be achieved through one or multiple steps to ensure the coherence of the multicellular body (e.g., cellular unit). In certain processes, upon the initial maturation, the cell paste may be partially stabilized, or partially hardened to form the multicellular body with integrity sufficient to allow further handling.

According to one embodiment, the forming step may include two substeps: A) retaining the cell paste in the shaping device, such as a micropipette (e.g., a capillary pipette), for a first time period (e.g., a pre-determined time period) for the initial maturation, and B) depositing the shaped cell paste into a holding device, such as a mold, for a second time period (e.g., a pre-determined time period) for further maturation, where the holding device is made of a material capable of excluding cells from growing or migrating into, or adherence onto it. The initial maturation will provide the cell paste with sufficient stability to remain intact during the handling in the further maturation process.

Various methods can be used to facilitate the further maturation process. In one embodiment, the cell paste may be incubated at about 37° C. for a time period (which may be cell-type dependent) to foster coherence. Alternatively or in addition, the cell paste may be held in the presence of cell culture medium containing factors and/or ions to foster adherence.

For example, after a cell paste in a cylindrical shape is incubated in a micropipette (e.g., a capillary pipette) (i.e., the initial maturation process) until the adherence of the cells is such that the cylinder can be extruded without breakage from the micropipette, the cell paste may then be further incubated and cultured with medium in the further maturation process, which encourages retention of the desired shape.

Filler Bodies

The present invention also provides filler bodies which can be used in combination with the above-described multicellular bodies to form desired three-dimensional biological engineered tissues. The filler bodies are described at length at paragraphs [0097]-[0104] of U.S. Patent Application Publication No. 2010/0041134. Briefly, the present invention also provides a filler body to be used in combination with the multicellular bodies as building units for constructing a biological construct, where the filler bodies are used to define the domains of the desired three-dimensional bioconstruct that are devoid of multicellular bodies (e.g., to define acellular channels in the multicellular constructs). The filler body is suitably a body having a pre-determined shape made of an acellular material capable of excluding at least some types of cells from growing or migrating into or adhering to it. In some embodiments, the filler bodies are made of a material (e.g., agarose) that excludes most cell types from migrating into the filler bodies but which can be left in place in the acellular channels of the mature axon-guiding graft and which permits the growth of axons from the proximal nerve structure into and through the axon-guiding graft. The filler body material is suitably permeable to nutrient media (also referred to herein as tissue culture medium or cell culture medium). For example, the filler body material is suitably a biocompatible gel material selected from the group consisting of agarose, hyaluronic acid, polyethylene glycol, and agar, or other hydrogel or a non-gel flexible biocompatible material. All of the filler bodies to be used in constructing a particular three-dimensional biological engineered tissue can suitably be formed from the same material and from the same concentration of the same material. For example, the filler bodies can suitably be made of agarose at a concentration of about 0.5% to about 4.5%, more suitably can be made of agarose at a concentration of about 1.5% to about 4%, and still more suitably can be made of agarose at a concentration of about 2%. As another example, the filler bodies can suitably be formed from different materials or from different concentrations of the same material. For instance, a lumen-forming filler body can be made of 4% agarose, while the remaining filler bodies used to construct a desired three-dimensional biological engineered tissue can be made of 2% agarose. The filler body may assume any shape or size in accordance with the shape or size of the corresponding multicellular body, with a cylindrical shape as preferred.

In some embodiments, the filler bodies have shapes and sizes substantially identical to the shapes and sizes of the multicellular bodies with which they are to be used to build a desired three-dimensional biological engineered tissue. Thus, for example, the filler bodies can suitably have any of the shapes described above in connection with the multicellular body 1. For example, both the filler bodies and the multicellular bodies may be substantially cylindrical (e.g., substantially rod-shaped) and have substantially circular cross-sections having substantially identical diameters (as shown in FIG. 1).

Figure 8:
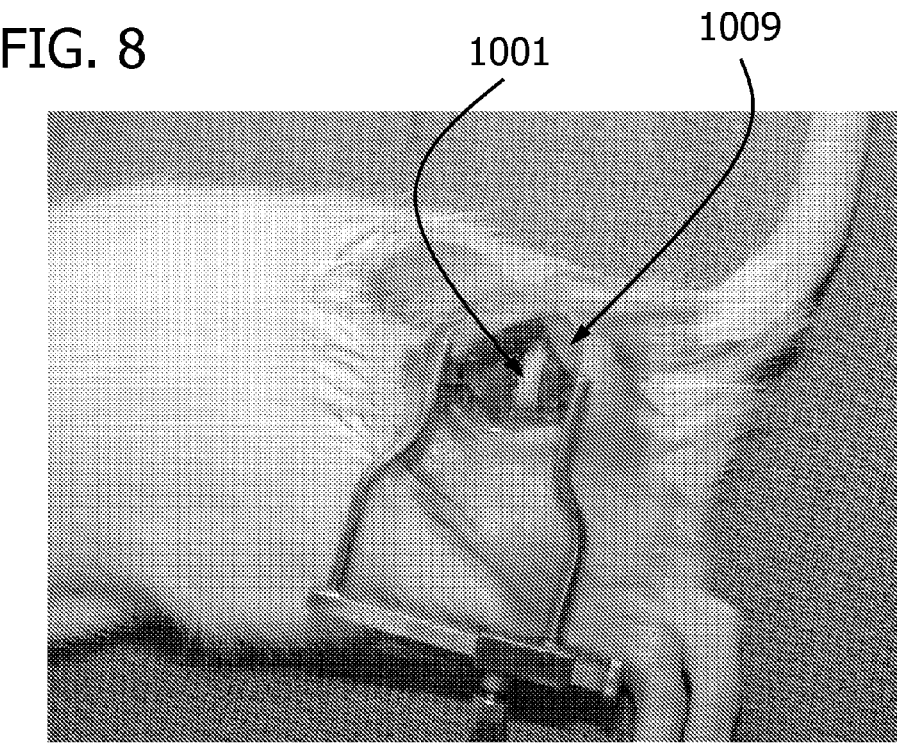
FIGS. 8 and 9 are photographs showing surgical fields in rats following implantation of axon-guiding grafts engineered according to the methods described herein.
Figure 12:
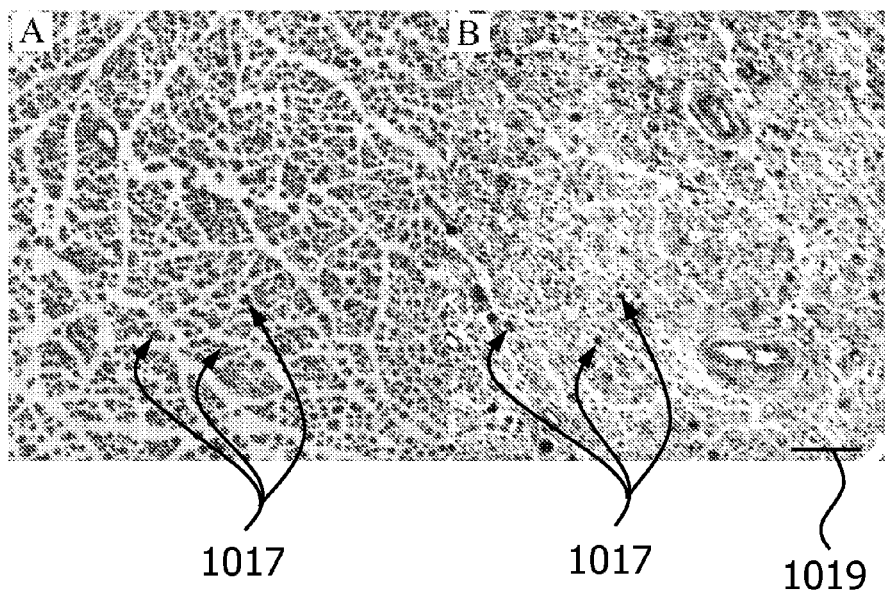
FIG. 12 includes two histological photographs of transverse sections taken from the proximal native nerve (left) and the distal native nerve (right) following a three-week implantation in a rat with an axon-guiding graft engineered according to the methods described herein.

Although the filler bodies 1 illustrated in FIGS. 1 and 2 are substantially cylindrical and have a substantially circular cross-section, filler bodies having different sizes and shapes are also within the scope of the invention, so long as the filler bodies and multicellular bodies can be arranged according to a pattern such that a desired three-dimensional biological engineered tissue is formed when the multicellular bodies fuse to one another. For instance, the filler bodies can be substantially cylindrical (e.g., substantially rod-shaped) and the multicellular bodies can be substantially spherical (as illustrated in FIGS. 8 and 12 of U.S. Patent Application Publication No. 2010/0041134). Further, the filler bodies and the multicellular bodies may both be elongate and substantially cylindrical, but have different lengths. The skilled artisan will recognize that there are many ways in which filler bodies and multicellular bodies of varying sizes and shapes can be combined to form a desired three-dimensional biological engineered tissue.

The filler bodies are suitably produced using the methods described in paragraphs [0100] through [0104] of U.S. Patent Application Publication No. 2010/0041134.

Three Dimensional Structures

The multicellular bodies and filler bodies described above can be used in accordance with the methods of the present invention to produce a three-dimensional biological engineered tissue, such as an axon-guiding nerve graft. Briefly, a plurality of multicellular bodies and a plurality of filler bodies are arranged according to a pattern such that each multicellular body contacts at least one of (i) another multicellular body, or (ii) a filler body. The multicellular bodies are then allowed to fuse with at least one other multicellular body through a maturation process to form a there-dimensional biological engineered tissue graft suitable for use in nerve restoration procedures. The filler bodies can then be separated from the fused multicellular bodies to obtain the engineered tissue graft, but in some embodiments the graft can include one or more filler bodies that are left in place through implantation.

One embodiment of a three-dimensional structure of the present invention, which is generally designated 101, is illustrated in FIGS. 1 and 2. The structure 101 includes a plurality of elongate multicellular bodies 1, each of which is suitably identical to the elongate multicellular body 1 described above. For example, each of the elongate multicellular bodies 1 has suitably been produced according to the methods described above for producing a self-supporting multicellular tissue body that can be printed in air. The multicellular bodies 1 are arranged in a pattern in which each multicellular body contacts at least one other multicellular body. At least one of the multicellular bodies 1 contacts another of the multicellular bodies along a contact area that has a substantial length. This contact between the multicellular bodies over a substantial length is described in greater detail in U.S. Patent Application Publication No. 2010/0041134 at paragraph [00106] and is illustrated in FIG. 1C of that publication. For example, in the arrangement of FIGS. 1 and 2 each of the multicellular bodies 1 contacts at least one (e.g., two) other multicellular bodies over a contact area having a substantial length. The contact area between adjoining elongate multicellular bodies in side-by-side adjoining relation suitably has a length of at least about 1 centimeter. The length of the contact area can correspond to the length of the multicellular bodies 1, which is suitably about equal to the length of the graft that is desired. Although the multicellular bodies 1 are in contact with one another in FIGS. 1 and 2, at this initial stage of maturation the multicellular bodies are not cohered to one another.

The structure 101 also includes one or more filler bodies 5, each of which is suitably identical to the filler body described above. For example, the structure in FIGS. 1 and 2 includes a plurality of discrete filler bodies 5. The filler bodies 5 are arranged in the pattern with the multicellular bodies so each filler body contacts at least one multicellular body 1 or another filler body. The multicellular bodies 1 and filler bodies 5 in FIGS. 1 and 2 are arranged to form a plurality of spaces 17 in the structure 101 that are not occupied by the multicellular bodies and also not occupied by the filler bodies. The spaces 17 can suitably contain tissue culture medium, which can be added to the structure 101 by pouring the tissue culture medium over the top of the multicellular bodies 1 and filler bodies 5. Thus, the spaces 17 can facilitate supply of nutrients and/or oxygen to the cells in the multicellular bodies 1 (e.g., during maturation).

At least some of the multicellular bodies 1 in the structure are heterocellular bodies containing Schwann cells, as described above. For example, the heterocellular bodies suitably include Schwann cells in combination with cells of a different cell type having one or more anti-inflammatory properties, such as bone marrow stem cells or mesenchymal stem cells. The Schwann cell-containing heterocellular bodies form a first set of multicellular bodies, which are designated 1". The multicellular bodies in the structure also include a second set of multicellular bodies, which are designated 1' in which the percentage of cells that are Schwann cells is less than the percentage of cells in the first set of multicellular bodies that are Schwann cells. For example, the multicellular bodies in the second set 1' can be homocellular bodies (e.g., containing substantially only BMSCs) or heterocellular bodies (e.g., including BMSCs and a relatively low number of Schwann cells).

At least some of the multicellular bodies 1 of the second set 1' (e.g., those having few or no Schwann cells) are arranged to form the outer layer of a tube-like structure 31. At least one of the filler bodies 5 and at least one of the multicellular bodies of the first set 1" (e.g., those having a relatively higher percentage of Schwann cells) are inside the outer layer of the tube-like structure 31 and substantially surrounded by the multicellular bodies that form the outer layer of the tube-like structure. For example, the multicellular bodies 1' in FIGS. 1 and 2 are arranged in a hexagonal configuration to form a tube-like structure 31 surrounding three filler bodies 5 and three of the Schwann cell containing multicellular bodies 1". Each of the multicellular bodies 1' in the hexagonal configuration is in side-by-side adjoining relation with at least two neighboring elongate multicellular bodies 1. In this arrangement, the one or more filler bodies 5 inside the tube-like structure 31 are positioned to form a plurality of acellular channels extending through the structure 101. The filler bodies 5 suitably prevent migration and ingrowth of cells from the multicellular bodies 1 into an elongate space that extends through the tube-like structure 31, which becomes an acellular channel after maturation of the structure according to the methods described below. In general, any arrangement of multicellular bodies 1 that can via maturation produce a tubular engineered tissue that includes a plurality of living cells can be considered a tube-like structure whether or not there are filler bodies inside the tube-like structure. It is apparent from the foregoing that the tube-like structure can differ from a tubular structure by virtue of the fact the adjoining multicellular bodies are not cohered to one another at this stage of maturation so an object could be pushed into the space between two of the adjoining multicellular bodies forming the tube-like structure.

FIG. 1A illustrates another embodiment of a three-dimensional structure, generally designated 101". Except as noted, this structure 101" is identical to the structure 101 described above and illustrated in FIG. 1. This structure 101" does not include any filler bodies 5 within the tube-like structure 31. Instead, the tube-like structure is substantially filled with the Schwann cell containing multicellular bodies 1".

Methods of Making Three-Dimensional Structures

There are many different ways to use the multicellular bodies described above, including the elongate multicellular bodies 1 in conjunction with the filler bodies 5 to produce the three-dimensional biological constructs described above within the scope of the invention. For example, one method generally involves arranging a plurality of elongate multicellular bodies 1 according to a pattern such that each of the multicellular bodies contacts at least one other multicellular body and then allowing at least one (e.g., all) of the multicellular bodies to fuse to at least one other multicellular body to produce a desired three-dimensional biological engineered tissue A number of methods may be used to deliver the multicellular bodies in a pre-determined pattern to produce the desired three-dimensional structure. For example, the multicellular bodies can be manually placed in contact with one another or a filler body, deposited in place by extrusion from a pipette, nozzle, or needle, or positioned in contact by an automated machine. For example, one or more implements (which can suitably include the first shaping device 51 described above, the capillary pipette that takes the multicellular body out of the mold 301, as described above, and/or a different implement) is used to pick up a multicellular body (e.g., to take them out of the mold 301 described above). The implement transports the multicellular body to an assembly area (for example, a glass surface) where a three-dimensional construct is being assembled (e.g., as illustrated in FIG. 2) and dispenses or otherwise places the multicellular body in position relative to any other multicellular bodies and any filler bodies that have already been transported to the assembly area and placed in the construct that is being assembled.

After each multicellular body 1 has been placed in its position, the process is suitably repeated to add another multicellular body or a filler body to the construct (e.g., by placing it alongside a multicellular body that has already been placed in the construct). If the construct that is being assembled includes one or more filler bodies, another implement (which is not shown, but which may be similar to the shaping device 51 or capillary pipette) is suitably used to pick up a filler body 5 (or make a filler body, as described above), transport the filler body to the assembly area, and dispense or otherwise place the filler body in its position within the construct that is being assembled whenever a filler body is needed. The implement used to transport multicellular bodies to the assembly area is suitably carried by a printing head of a bioprinter or other automated apparatus operable to arrange the multicellular bodies and filler bodies in a desired pattern. For example, one suitable bioprinter is disclosed in U.S. Patent Application Publication No. 2004/0253365, which is hereby incorporated by reference. The Novogen's MMX BIOPRINTER is one commercial embodiment of a suitable bioprinter. Those skilled in the art of tissue engineering will be familiar with other suitable bioprinters and similar apparatus that can be used to arrange the multicellular bodies (and filler bodies if they are used) into a suitable construct. The implement used to transport filler bodies to the assembly area is suitably part of another head of the bioprinter. A bioprinter can have multiple heads and/or the various implements for transporting the multicellular bodies and filler bodies can be loaded sequentially into one or more bioprinter heads. Although it may be desirable to use a bioprinter or similar apparatus to assemble the construct automatically, the methods described herein can be performed manually (e.g., using one or more capillary pipettes) within the scope of the invention.

As indicated in FIG. 2, the multicellular bodies 1 are suitably placed (e.g., stacked) on top of one or more filler bodies 5. The multicellular bodies 1 are suitably placed adjacent the other multicellular bodies and/or filler bodies 5. Thus, the multicellular bodies 1 are not pushed into or embedded in any of the filler bodies 5. This can be referred to as "printing in air" because the multicellular bodies are not dispensed into a gel or liquid.

Once assembly of the construct is complete, a tissue culture medium is suitably poured over the top of the construct. The tissue culture medium can enter the spaces 17 between the multicellular bodies and the filler bodies to support the cells in the multicellular bodies. Additional filler bodies (not shown) can be stacked around the structure illustrated in FIG. 2 to provide further support to help hold the filler bodies and multicellular bodies in position relative to one another as the structure is incubated and allowed to mature.

Figure 2A:
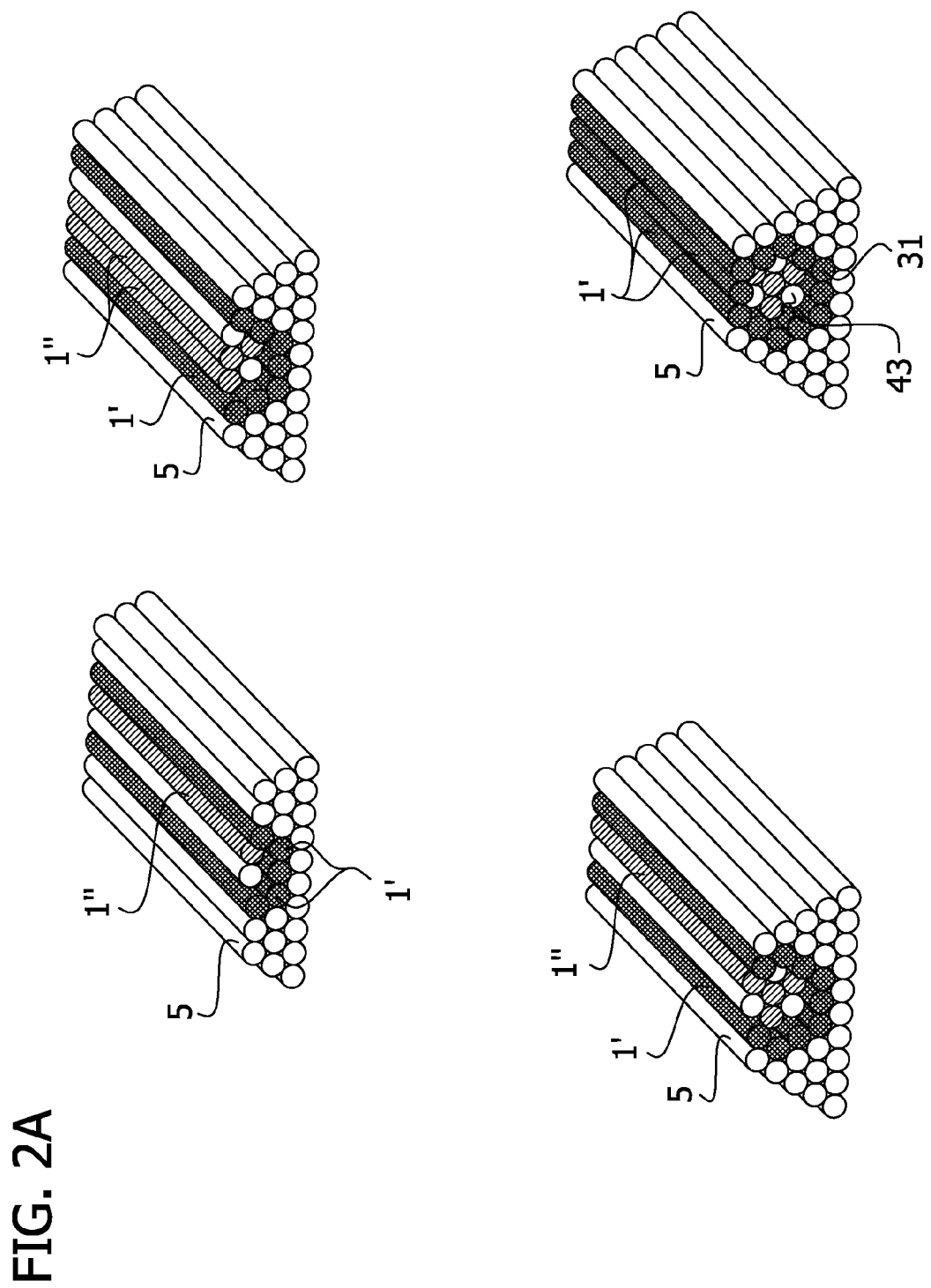
FIG. 2A illustrates another embodiment of a sequence in which multiple muticellular bodies and filler bodies are stacked on top of one another according to a predetermined pattern to form a three-dimensional structure.
Figure 2C:
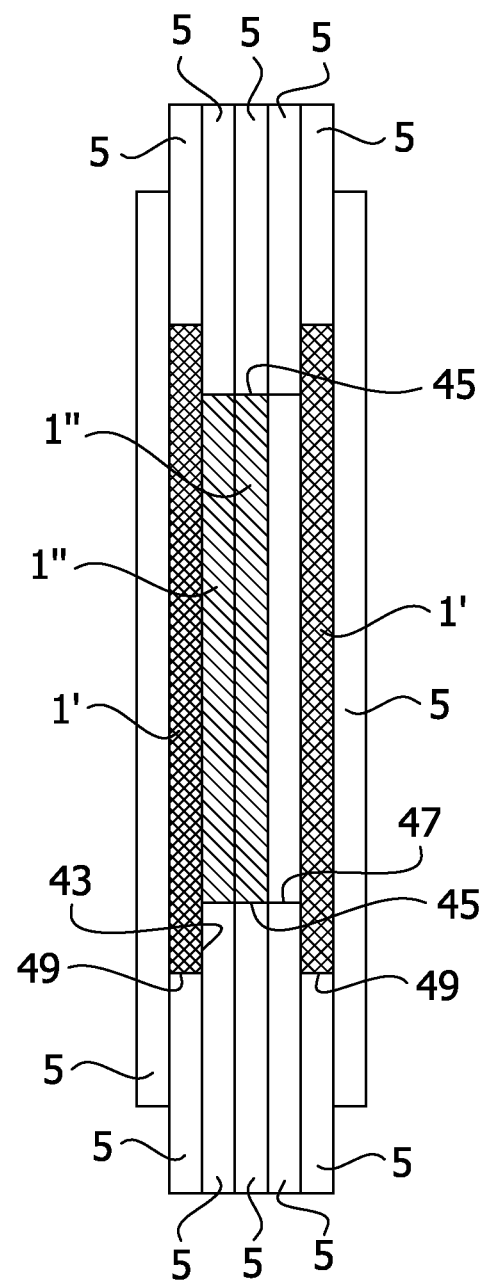
FIG. 2C is a top plan view of the three-dimensional construct produced according to the sequence illustrated in FIG. 2A in combination with additional filler bodies stacked at the end of the construct for additional stability.

FIGS. 2A and 2B illustrate a method of making a structure that is substantially similar to the structure 101 in FIG. 2, except the filler bodies and multicellular bodies 1" inside the tubular construct are slightly shorter in length than the multicellular bodies forming the tube-like structure. This creates a recessed area 43 at the opposite ends of the structure. Additional filler bodies 5 (FIG. 2C) are stacked around the structure and extend into the recesses 43 at the ends of the structure so some of the multicellular bodies overlap the gaps or joints where the end of one filler body or multicellular body abuts the end of another. In particular, as illustrated in FIG. 2C, the recessed ends 45 of the multicellular bodies 1" and filler bodies 5 are axially offset from the ends 49 of the multicellular bodies 1' forming the tube-like structure 31. Some of the filler bodies 5 have ends 47 that extend into the recess 43 and abut the recessed ends 45 of the filler bodies and multicellular bodies 1" forming the recess. The multicellular bodies 1' that form the outer tube-like structure have sufficient length to overlap the abutting ends 45, 47. This makes the three dimensional structure more stable. The filler bodies at the recessed ends provide support as the construct is being built. The ends of the graft formed by this structure allow a surgeon to place the graft correctly without touching the graft itself, and can also provide a border for attaching the graft to the ends of the native nerve structure. Alternatively, the ends of the graft can be cut off before implantation.

The multicellular bodies in the three-dimensional construct are allowed to fuse to one another to produce a biological engineered tissue. By "fuse," "fused" or "fusion", it is meant that the cells of contiguous multicellular bodies become adhered to one another, either directly through interactions between cell surface proteins, or indirectly through interactions of the cells with ECM components or derivatives of ECM components. After fusion, any filler bodies that surround the construct are suitably separated from the engineered tissue. In the case of a construct that includes a tube-like structure, for example, any filler bodies outside of the tube can be removed (e.g., by peeling them away from the tubular structure formed from the tube-like construct).

The filler bodies 5 inside the tubular structure can suitably be left in place. In other cases, filler bodies 5 can be removed from the three-dimensional construct following maturation and prior to implantation, as will be discussed further below. In cases where the filler bodies 5 are removed, this can suitably be accomplished by pulling them out of an open end of the tubular structure. In addition, if filler bodies 5 are to be removed from the structure following maturation, the filler bodies 5 can suitably be made of a flexible material if desired to facilitate pulling the filler bodies out of the structure. Another option is to make the filler bodies 5 from a material that can be dissolved (e.g., by temperature change, light, or other stimuli) after fusion.

The present invention further provides another method of engineering a biological construct with a 3-D shape, such as a tissue (e.g., an axon-guiding graft), using the multicellular bodies by further delivering a plurality of multicellular bodies according to a pre-determined 3-D pattern in a pre-selected receiving environment, so that the cellular units may fuse into the desired bio-construct. The two or more multicellular bodies that are fused may be of identical or differing shapes and sizes, and may contain the same or differing cell types. The multicellular bodies may be applied in bio-construct-engineering in number of ways. For example, two differently shaped multicellular bodies comprising a top half and a bottom half of a desired structure may be produced, and may be brought into contact and allowed to fuse. Alternatively, a plurality of multicellular bodies may be assembled and allowed to fuse into a desired shape, in combination with filler bodies. According to one embodiment, when the multicellular bodies are employed with the filler bodies, the engineering method may comprise the steps of A) delivering the plurality of multicellular bodies in a pre-determined combination with a plurality of filler bodies according to the pre-determined pattern to form a layered construct, whereby the multicellular bodies and the filler bodies are contiguous, B) depositing the layered construct into a pre-selected controlled environment for maturation, whereby the multicellular bodies fuse with each other to result in a fused construct, and C) removing the filler bodies from the fused construct to produce the desired biological construct.

Axon-Guiding Graft for Repairing a Damaged Nerve

Figure 5:
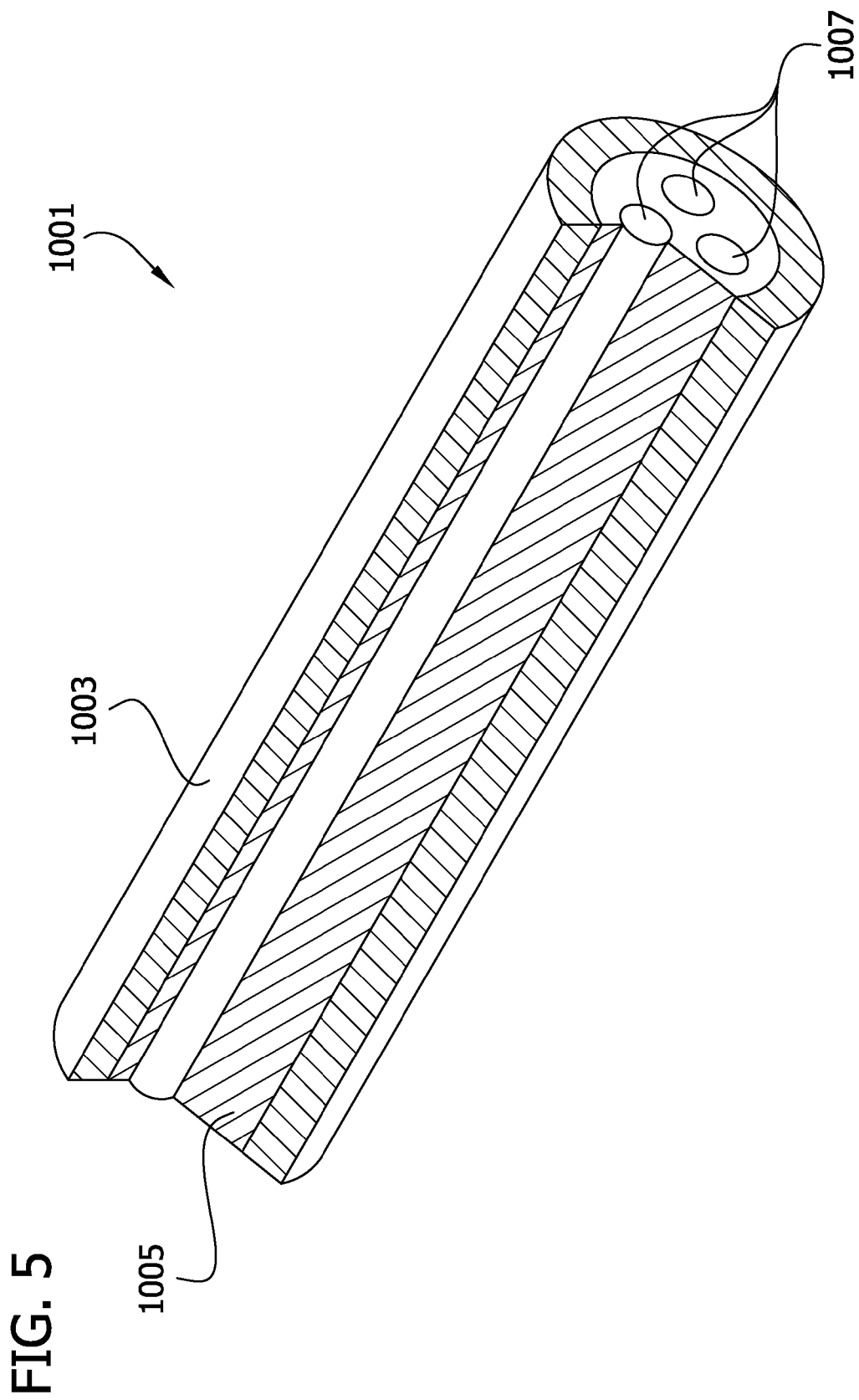
FIG. 5 is a schematic perspective of one embodiment of an axon-guiding graft with a portion of the graft removed to show internal features thereof.

FIG. 5 illustrates one example of a multicellular construct (e.g., axon-guiding graft), generally designated 1001, engineered according to the methods of the invention. As illustrated, the construct includes an elongate multicellular region including a central portion 1005 and a peripheral portion 1003. Each portion 1003, 1005 of the multicellular region comprises a plurality of living cells cohered to one another so the multicellular region forms an elongate graft 1001 suitable for use in restoration of nerve function to damaged nerves. As will be explained in more detail below, the graft 1001 is adapted to promote regenerative axon growth through the graft when the graft is implanted in a living organism having a nervous system and positioned in a gap between the ends of a severed nerve (e.g., wherein the nerve has been severed by traumatic injury and/or resected by a health care practitioner in preparation for a nerve restoration procedure). The graft 1001 is a tubular structure in the broad sense. However, the graft does not have to have any particular cross-sectional shape and is not required to have any hollow parts within the broad scope of the invention.

The multicellular region comprises the same types of cells described above in connection with the description of the multicellular bodies. For example, the multicellular region suitably comprises cells selected from the group consisting of mesenchymal stem cells, bone marrow stem cells, hair follicle stem cells, olfactory ensheathing cells, fibroblasts, smooth muscle cells, Schwann cells, and combinations thereof. In another example, the cells in the multicellular region comprise cells having one or more anti-inflammatory properties, such as bone marrow stem cells. In yet another example, the cells in the multicellular region comprise Schwann cells. In still another example, the cells in the multicellular region comprise bone marrow stem cells and Schwann cells in combination. When the multicellular region includes Schwann cells, the number of Schwann cells is suitably in the range of about 0.1 percent (v/v) to about 20 percent (v/v), more suitably in the range of about 1 percent (v/v) to about 15 percent (v/v), and still more suitably in the range of about 3 percent (v/v) to about 10 (v/v) percent, and even still more suitably about 5 percent (v/v) to about 10 (v/v) percent, of the total number of cells in the multicellular region. Also, when the multicellular region includes Schwann cells, the other living cells in the multicellular region can suitably consist essentially of bone marrow stem cells. It is understood, however, that various combinations of cell types other than those set forth in the specific examples recited above may be present within the multicellular region of the graft within the broad scope of the invention.

In the embodiment illustrated in FIG. 5, at least one acellular channel 1007 extends axially through the interior of the graft 1001 between opposite ends of the structure formed by the multicellular region. More particularly, in FIG. 5 a plurality of discrete acellular channels 1007 extend through the graft 1001 between opposite ends of the structure formed by the multicellular region. The number of acellular channels 1007 can vary within the broad scope of the invention. For example, there are suitably between 2 and 7 acellular channels, and more suitably between 3 and 5 acellular channels. In another example, there are at least three acellular channels. For example, the graft 1001 illustrated in FIG. 5 has exactly three acellular channels 1007. The acellular channels 1007 suitably extend all the way through the graft 1001 so each of the channels can extend substantially continuously all the way between the opposing proximal and distal nerve stubs when the graft is implanted. However, the acellular channels can be slightly shorter in length than the overall length of the graft within the scope of the invention. For example, the outer peripheral portion 1003 of the graft can be made slightly longer than the central portion 1005 (including acellular channels in the central portion), for example by using the methods outlined in FIGS. 2A and 2B. If desired, the ends of the graft having a longer outer portion can be cut off to ready the graft for implantation. As noted above, it is also possible to implant the graft while the ends are uneven within the scope of the invention.

The acellular channels 1007 are suitably arranged in a side-by-side orientation and separated from one another by the cells in the multicellular region, as illustrated in FIG. 5. For example, the acellular channels 1007 are suitably substantially parallel with one another. Further, the acellular channels 1007 are suitably spaced from one another by a section of the multicellular region. The acellular channels 1007 are also suitably spaced evenly from one another. The thickness of the section of the multicellular region between the channels will vary depending on the number of channels and the diameter of the channels.

that has sufficient thickness to support the Schwann cell rich lining of the acellular channels.

The acellular channels 1007 are suitably formed by the filler bodies 5. The dimensions of the acellular channels 1007 can suitably be substantially identical to the dimensions for the filler bodies described above. Alternatively, the acellular channels 1007 can be of a different length than the filler bodies 5. For example, two (or more) filler bodies can be placed end to end to create one acellular channel which is longer than the individual filler bodies. In some cases the filler bodies 5 can be removed from the graft 1001 before implantation at the site of the damaged nerve. If the filler bodies 5 are removed, the acellular channels 1007 are empty when the graft 1001 is implanted and form hollow axon guides that guide axon growth from the proximal nerve stump through the graft to the distal nerve stump. In other cases, one or more filler bodies 5 may remain in the three dimensional construct/graft 1001 and be implanted with the rest of the graft at the damaged nerve site. For example, it has been found that when the filler bodies 5 are made of agarose and are left in place in the acellular channels of a mature axon-guiding graft for implantation, axons from the proximal nerve structure grow into and through the axon-guiding graft. In this case, the filler body 5 also provides additional mechanical integrity to the graft 1001 and helps prevent collapse of the acellular channels 1007 if the graft is compressed either before or after implantation.

Schwann cells suitably populate at least portions of the interfaces between the acellular channels 1007 and the multicellular region of the graft 1001. In particular, at least some of the Schwann cells suitably form a Schwann cell rich lining for the acellular channels 1007 for supporting axon ingrowth. As illustrated in 5, the graft has a central portion 1005 having a higher percentage of Schwann cells and a peripheral portion 1003 that surrounds the central portion and which has a lower percentage of Schwann cells. Although the boundary between the peripheral portion 1003 and the central portion 1005 is illustrated in the schematic view of FIG. 5 as being a distinct boundary, it is recognized the multicellular portion of the graft will not be distinct like this in practice, but instead there will be a gradual transition from the Schwann cell rich central portion to the peripheral portion which has relatively fewer or no Schwann cells. The Schwann cell rich central portion 1005 of the graft 1001 generally corresponds to the area formed by the multicellular filler bodies 1" containing the higher percentage of Schwann cells. The overall percentage of Schwann cells in the central portion 1005 of the graft 1001 is about equal to the percentage of Schwann cells in the Schwann cell containing multicellular bodies 1" described above. During maturation of the three dimensional construct 101 formed by the multicellular bodies 1', 1" and filler bodies 5, some of the Schwann cells sort themselves into the lining of the acellular channels 1007 in a manner that is consistent with Differential Adhesion Hypothesis' explanation of self sorting cell types. The Schwann cells preferentially move toward the lining of the acellular channels 1007, although other types of cells from the multicellular bodies 1', 1" may also be present in the lining within the scope of the invention. It is believed that the Schwann cell-rich lining of the acellular channels 1007 facilitates ingrowth of axons into the acellular channels of the graft 1001. Schwann cells are known to have roles in nerve development and regeneration. Without being bound to any particular theory, it is thought that the neurotrophic factors released by the Schwann cells and/or the transected axons in the damaged nerve may promote growth of axons from the proximal native nerve through the axon-guiding graft and into the distal end of the nerve. Because the Schwann cells are located along the surfaces of the acellular channels 1007, they are positioned to contact the axons and/or agarose filler bodies as the axons grow into the graft. Thus, signaling molecules released by the Schwann cells can promote axon growth through the graft.

It will be recognized from the foregoing that the graft 1001 is suitably an engineered tissue made by allowing the tissue construct 101 created by arranging the multicellular bodies and filler bodies in predetermined pattern, as described above, to mature in an incubator. As a result of using the methods described above, the three dimensional structure formed by the multicellular region is suitably non-innervated. Moreover, the three dimensional structure suitably comprises some residual tissue culture medium from the multicellular bodies. In contrast, many prior art grafts used for nerve repair (including autografts and allografts) are innervated. Further, prior art autografts and allografts do not include any tissue culture medium.

Figure 11:
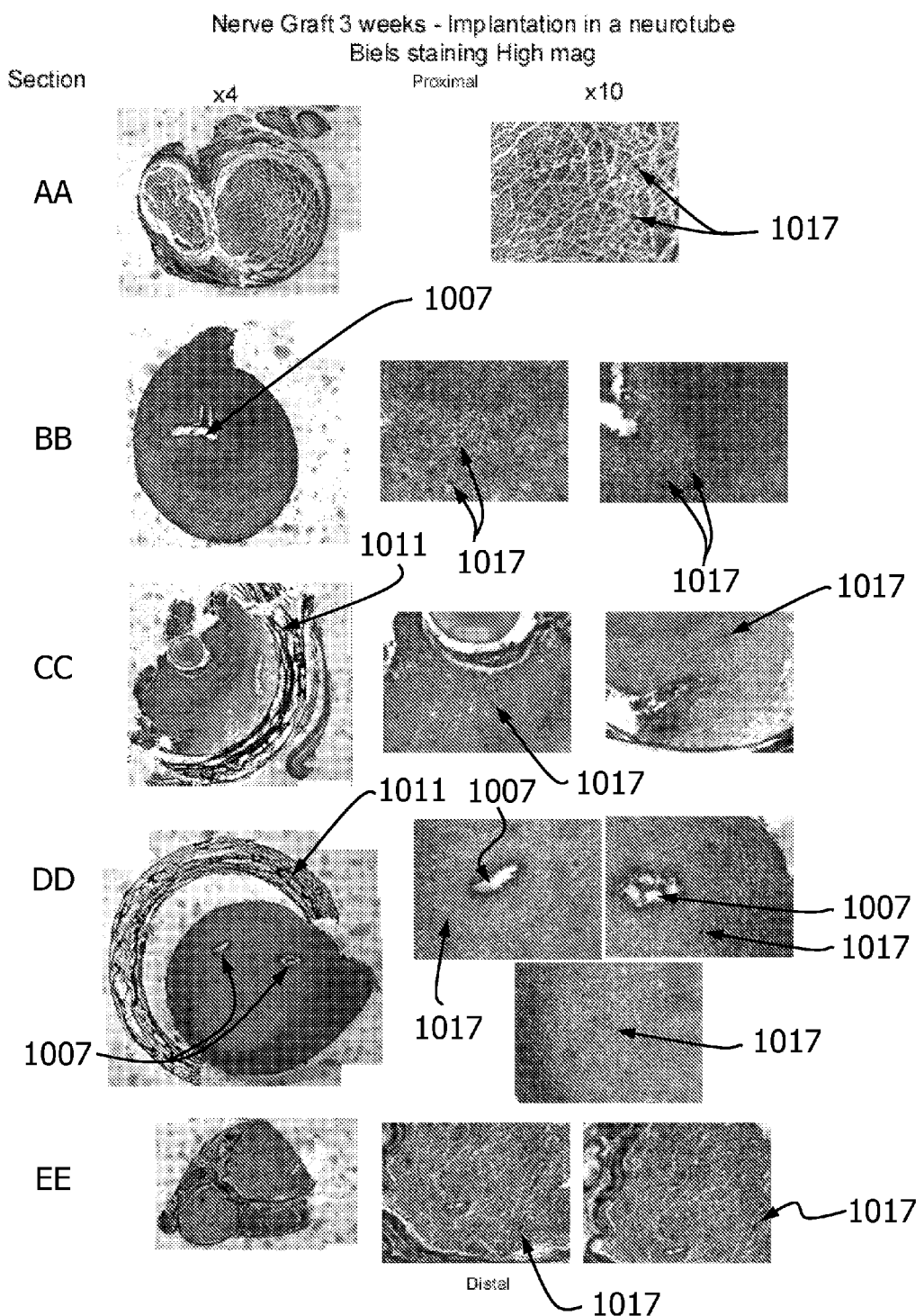
FIG. 11 includes a group of histological photographs of transverse sections taken from the nerve segment shown in FIG. 10, wherein the sections were taken along lines AA, BB, CC, DD, and EE, respectively, and the photographs in the left column of FIG. 11 are sized to show the entire cross-section of the graft, and to the right of the photos in the left column are enlargements of various features in the photograph in the left column.

In some embodiments, the axon-guiding graft does not include any acellular channels formed by filler bodies. It is believed that axons from the proximal native nerve will grow into and through an axon-guiding graft even without the acellular channels described herein. FIG. 11, which is described in more detail below, shows that following a three-week implantation with an axon-guiding graft which did include acellular channels occupied by filler bodies at the time of implantation, axons (the small black dots identified by reference number 1017), were present in many places in the graft outside of the portions of the acellular channels 1007 which remained in the graft at the end of the three-week implantation. This suggests axons were able to grow through the Schwann cell-rich central portion 1005, described above, from the proximal end to the distal end without growing through the filler bodies or growing through the acellular channels. Thus, it is likely that an axon-guiding graft which lacked the acellular channels described herein would also support the growth of axons from the proximal native nerve into and through the graft and into the distal end of the native nerve structure.

Repair of Damaged Nerves Using the Axon-Guiding Grafts

Following maturation, the axon-guiding grafts can be implanted into a living organism (e.g., a human or other animal) having an injury to a nerve. The axon-guiding graft can be positioned in a gap between the ends of a severed nerve. Positioning the axon-guiding graft in this manner promotes regenerative axon growth through the acellular channels of the axon-guiding graft and leads to restoration of nerve function. More particularly, axons from the proximal end of the severed native nerve grow through the acellular channels of the axon-guiding graft and into the distal end of the nerve structure.

Prior to implantation, the biocompatible gel material (e.g., agarose), which surrounds the axon-guiding graft 1001 is removed, leaving a structure such as the one illustrated in FIG. 5. The biocompatible gel material in the acellular channels 1007 may be left in place for implantation if it is a material which permits the growth of axons from the proximal nerve structure into and through the axon-guiding graft. For example, if agarose filler bodies 5 are used to create the acellular channels 1007, the agarose filler bodies do not need to be removed from the acellular channels prior to implantation, because it is known that axons will grow into and through the graft even when the agarose filler bodies are left in the acellular channels for implantation. Leaving the filler bodies 5 in the acellular channels 1007 can advantageously confer additional structural integrity to the graft. For example, the filler bodies can hold the acellular channels open even if the graft is compressed before or after implantation.

As another example, the filler bodies 5 in the acellular channels 1007 may be removed prior to implantation of the axon-guiding graft 1001. Removal of the filler bodies 5 in the acellular channels 1007 would be appropriate where, for example, the filler bodies are composed of a material which does not support the growth of axons. If the filler bodies 5 in the acellular channels 1007 are removed before implantation, the acellular channels are hollow at the time of implantation and become populated by axons over time as axons grow into the graft.

The inventive axon-guiding grafts can be used in the repair of any nerve in the peripheral nervous system which has been severed, either as the direct result of an injury or as the result of nerve resection surgery. The axon-guiding grafts can be constructed using the methods set forth above to be of a length suitable for the repair of a gap in a severed nerve ranging from at least about 1 cm to about 7 cm in length. The axon-guiding grafts are suitably constructed to have a length which is at least as long as the gap between the ends of the severed nerve to be repaired. Thus, for example, if the gap in the severed nerve is about 3 cm in length, the axon-guiding graft is suitably prepared to also be at least about 3 cm in length. It is much better for the graft to be too long than it is for the graft to be too short because a graft that is too long can easily be cut to length when the surgeon has the nerve exposed. Thus, the grafts are suitably constructed so they can be cut into a shorter segment any time before implantation is complete. The axon-guiding grafts are especially suitable for the repair of gaps in severed nerves of a length across which spontaneous regeneration of the nerve is unlikely to occur. Spontaneous regeneration usually only occurs when a gap in a severed nerve is less than about 3 cm in length, and does not always reliably occur even when the gap is in the severed nerve is 2 cm in length. Thus, the axon-guiding grafts are particularly suitable for the repair of a gap in a severed nerve of at least about 2 cm.

Thus, the axon-guiding grafts are suitable for the repair of gaps in severed nerves having a length in the range of about 1 cm to about 7 cm, are more suitable for the repair of gaps in severed nerves having a length in the range of about 2 cm to about 6 cm, and are still more suitable for the repair of gaps in severed nerves having a length in the rage of about 3 cm to about 5 cm.

Furthermore, it will be appreciated that by using the present technology to make an axon-guiding graft, the cross-sectional architecture of the graft can be constructed to match the cross-sectional architecture of the nerve to be repaired. In particular, the diameter of the axon-guiding graft can be varied, for example, by varying the diameters of the multicellular bodies and/or filler bodies, or by varying the number of multicellular bodies and or filler bodies used to construct the axon-guiding graft. In addition, more than one axon-guiding graft can be used to repair damage to a large-diameter nerve. Moreover, the number of acellular channels in the axon-guiding graft can be varied using the techniques described hereinabove in order to create axon-guiding grafts with architecture suitable for the fascicles of the damaged nerve in need of repair.

The axon-guiding graft may be implanted at the site of a severed nerve either alone or inside a support sleeve (e.g., a collagen conduit or a cadaveric decellularized nerve). Those skilled in the art will be able to select an appropriate support sleeve. In general, collagen conduits which are used in the art to repair damaged nerves by other techniques (e.g., using an autograft) are also suitable for use as support sleeves in connection with the inventive axon-guiding grafts described herein. For example, the NEUROGEN collagen conduit, sold by Integra Life Sciences, may be used.

The site of the severed nerve at which the axon-guiding graft is to be inserted can be exposed using standard surgical techniques known in the art. When the axon-guiding graft is implanted alone (e.g., without a collagen conduit), the axon-guiding graft is suitably floated onto the surgical field and secured as an interposition graft at each end with surgical adhesive (e.g., fibrin glue) or sutures. When the axon-guiding graft is to be implanted together with a support sleeve, for example a collagen conduit, the collagen conduit or other sleeve is suitably cut such that its length approximately matches the length of the axon-guiding graft to be implanted. The collagen conduit is also cut along its longitudinal axis. The axon-guiding graft is then suitably floated onto the surgical field and into the longitudinally cut conduit, and the longitudinal cut in the conduit is resealed. Alternatively, the axon guiding graft can be placed inside the longitudinally cut conduit and then transferred to the surgical field. The free ends of the native nerve structure can then suitably be entubulated into the conduit and secured with surgical adhesive or a surgical suturing material (e.g., 9-0 nylon). Once the axon-guiding graft has been secured to both ends of the severed nerve structure, the surgical field can be closed using standard surgical techniques known to those skilled in the art.

EXAMPLES

Example 1

Preparation of Multicellular Bodies

Mouse Bone Marrow Stem Cells. Mouse bone marrow stem cells (BMSCs) were isolated under the same conditions used by Eisenberg et al., *Bone Marrow Cells Transdifferentiate to Cardiomyocytes When Introduced into the Embryonic Heart*, Stem Cells 24:1236-45 (2006), which is incorporated by reference herein in its entirety. Briefly, whole bone marrow was isolated from the femurs of 8-12 week old wild-type ICR mice. After flushing the bones with Iscove's modified Dulbecco's medium (IMDM), bone marrow was repetitively passaged through a 20-gauge needle and filtered through a 40 µm nylon sleeve. The resulting cell suspension was washed and placed in bacterial grade Petri dishes with IMDM/20% fetal bovine serum (FBS) for four weeks, with fresh medium provided weekly. Following isolation, the mouse BMSCs were cultured in IMDM supplemented with 12% donor equine serum, 12% fetal calf serum, 1 mM hydrocortisone and 1.0× $10^5$ units/L of penicillin and streptomycin (BMSC medium). The cells were grown on 10 cm Petri dishes and incubated at 37° C., 5% $CO_2$. Twelve confluent Petri dishes were necessary to prepare one axon-guiding graft having an outer diameter of approximately 2.5 mm and a length of 3.5 cm.

Schwann Cells. Schwann cells (CRL-2765) were purchased from ATCC. The medium composition was Dulbecco's Modified Eagle Medium (DMEM) high glucose supplemented with 10% FBS and 1.0×$10^5$ units/L of penicillin and streptomycin (Schwann cell medium).

Preparation of the Agarose Mold.

Preparation of a 2% agarose solution. Two grams of Ultrapure Low Melting Point (LMP) agarose was dissolved in 100 ml of ultrapure water/buffer solution (1:1, v/v). The buffer solution can be PBS (Dulbecco's phosphate buffered saline 1×) or HBSS (Hanks' balanced salt solution 1×). The agarose solution was placed in a beaker containing warm water (over 80° C.) and left on the hot plate until the agarose dissolved completely. The agarose solution remains liquid as long as the temperature is above 36° C. Below this temperature a phase transition occurs, the viscosity increases, and finally the agarose forms a gel.

Preparation of the agarose mold. An agarose mold was formed using a teflon print (i.e., a Teflon tool 201) (FIGS. 4A-C) that fits into a cell culture dish 221 (10 cm diameter). The assembly (Teflon tool+Petri dish) was maintained vertically and about 40 ml of pre-warmed agarose was poured into the Petri dish through a hole in the Teflon tool. After removing all air bubbles, the assembly was placed at 4° C. for at least 1 hour. After complete gelification of the agarose, the Teflon tool 201 was removed and grooves were visible in the agarose (see the grooves 305 in FIG. 4C). 10 ml of medium was then added to the mold.

Preparation of Multicellular Bodies.

BMSC multicellular bodies. The medium was removed from confluent Petri dishes of BMSCs and the cells were washed with 10 ml of PBS. 1.5 ml of trypsin 0.1% was spread evenly on the cells to detach the cells from the surface. When the cells started to detach from the dish, 5 ml of a 2 mM $CaCl_2$ solution in BMSC medium was added to the dish. The resulting cell suspension was centrifuged at 900 g for 5 minutes. After removal of the medium (i.e., removal of the supernatant), the cell pellet was resuspended in 200 µl of BMSC medium containing 2 mM $CaCl_2$ and pumped up and down with a pipette (i.e., vigorously pipetted) several times to break up cell clusters and obtain a substantially uniform cell suspension.

For preparation of substantially rod-shaped BMSC multicellular bodies, the cell suspension was transferred to a 2 ml Eppendorf tube placed inside a 15 ml centrifuge tube. A high-density pellet was formed by centrifugation at 1300 g for 2 minutes. The medium (i.e., the supernatant) was removed and the pellet (i.e., the cell paste) was transferred by aspiration into capillary tubes (outer diameter (OD)=1 mm; inner diameter (ID)=0.5 or 0.3 mm) inserted into 1 ml tips mounted on a 1 ml Eppendorf pipettor. The capillary tubes containing the cell paste were incubated in medium containing 2 mM $CaCl_2$ for 15 minutes at 37° C., 5% $CO_2$. The resulting shaped cell paste 55 was extruded as a substantially rod-shaped body from the capillary tubes 51 with the plunger into the grooves 305 of an agarose mold 301 filled with medium, as shown in FIG. 3C. The mold 301 was placed in the incubator overnight. The next day, the mature substantially rod-shaped BMSC multicellular bodies 1 were aspirated (i.e., sucked back) manually into capillary tubes 51' and placed into medium until further use, as shown in FIG. 3D.

(B) Mixed BMSC and Schwann cell multicellular bodies. The medium was removed from confluent Petri dishes of Schwann cells and the cells were washed with 10 ml of PBS. 1.5 ml of trypsin 0.1% was spread evenly on the cells to detach the cells from the surface. When the cells started to detach from the dish, 5 ml of Schwann cell medium was added to the dish. The resulting cell suspension was centrifuged at 900 g for 5 minutes. BMSCs were detached from confluent Petri dishes, resuspended in 5 ml of a 2 mM $CaCl_2$ solution in BMSC medium, and centrifuged at 900 g for 5 minutes, as described above. To create substantially rod-shaped multicellular bodies comprising both BMSCs and Schwann cells, the volumes of the cell pellets were estimated. A cell suspension containing approximately 90% BMSCs and approximately 10% Schwann cells (v/v) was prepared in 200 µl of BMSC medium and centrifuged at 1300 g for 2 minutes to create a high density cell pellet. The multicellular bodies containing both BMSCs and Schwann cells were prepared from this high density pellet according to the procedures described above.

Example 2

Preparation of a Bioengineered Axon-guiding Graft Having Three Acellular Channels Ten milliliters of a pre-warmed solution of 2% agarose was deposed in a 10 cm Petri dish and evenly spread to form a uniform layer. The Petri dish was placed at 4° C. to cause the agarose to gel. Capillary tubes were filled with a 2% agarose solution and cooled down (using cold blowing air or a cold PBS solution) to form substantially rod-shaped filler bodies.

Under a binocular microscope, a filler body 5 was extruded from the capillary tube 51, 51' using a piston or wire, and a 5 cm long agarose rod (i.e., filler body) was laid down straight on the agarose layer inside the Petri dish. Referring to FIGS. 1 and 2, a second filler body 5 was juxtaposed to (e.g., placed next to) the first one and so on until 10 filler bodies were deposited to form the first layer of the structure. The six filler bodies 5 present in the second layer of the structure were deposited as shown in FIGS. 1 and 2. Three BMSC multicellular bodies 1' were deposited at the fourth, fifth, and sixth positions of the second layer of the structure to form the bottom layer of the axon-guiding graft. The third layer of the structure was formed by the deposition of five filler bodies 5 at the first, second, fourth, seventh, and eighth positions, as shown in FIGS. 1 and 2, two BMSC multicellular bodies 1' at the third and sixth positions, and a mixed BMSC/Schwann cell multicellular body 1" at the fifth position. In the fourth layer of the structure, three filler bodies 5 were deposited at the first, fifth, and seventh positions, two BMSC multicellular bodies 1' were deposited at the second and sixth positions, and two mixed BMSC/Schwann cell multicellular bodies were deposited at the third and fourth positions 1". The fifth layer of the structure was composed of three filler bodies 5 (at the first, third, and sixth positions), two BMSC multicellular bodies 1' (at the second and fifth positions), and one mixed BMSC/Schwann cell multicellular body 1" (at the fourth position). To form the sixth layer of the structure, two agarose filler bodies 5 were deposited at the first and fifth positions, and three BMSC multicellular 1' bodies were deposited at the second, third, and fourth positions to form the top layer of the axon-guiding graft. The seventh layer was composed of four agarose filler bodies 5. Throughout the deposition process, small amounts of tissue culture medium (about 10 μl at a time) were added on the side of the construct to avoid dehydration of the material (i.e., the agarose and the multicellular bodies). Agarose filler bodies were placed on top of the construct in an orientation perpendicular to the filler bodies and multicellular bodies used to construct the structure described above and illustrated in FIG. 1, and 0.5 to 1 ml of liquid agarose was poured around the structure in order to maintain the integrity of the construct. After gelification, tissue culture medium was added until the entire construct was totally submerged. The construct was placed in the incubator for a 10 to 14 days maturation period, and the tissue culture medium was changed every other day.

Figure 6:
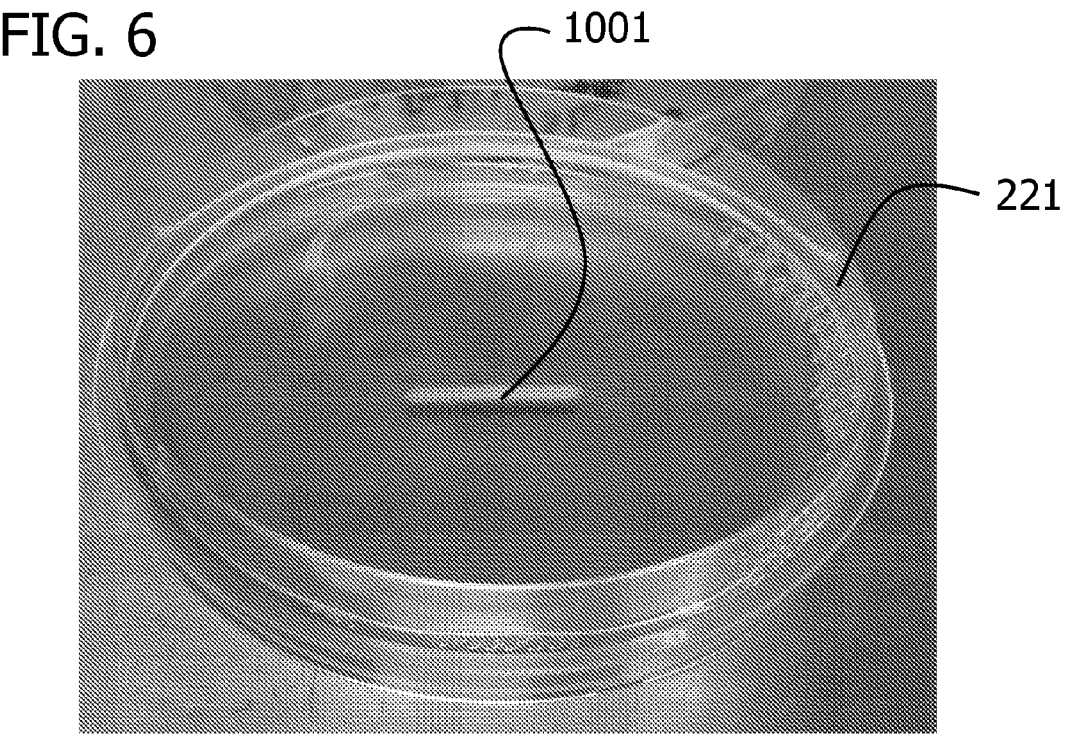
FIG. 6 is a photograph of one embodiment of an axon-guiding graft.

After 14 days, the agarose surrounding the axon-guiding graft was removed and the graft was sturdy enough to sustain suture and implantation. FIG. 6 is a photograph of an axon-guiding graft prepared using the above procedure in a 10 cm cell culture dish 221, following a 14 day maturation period.

Example 3

Localization of Schwann Cells in the Bioengineered Axon-guiding Graft

Figure 7:
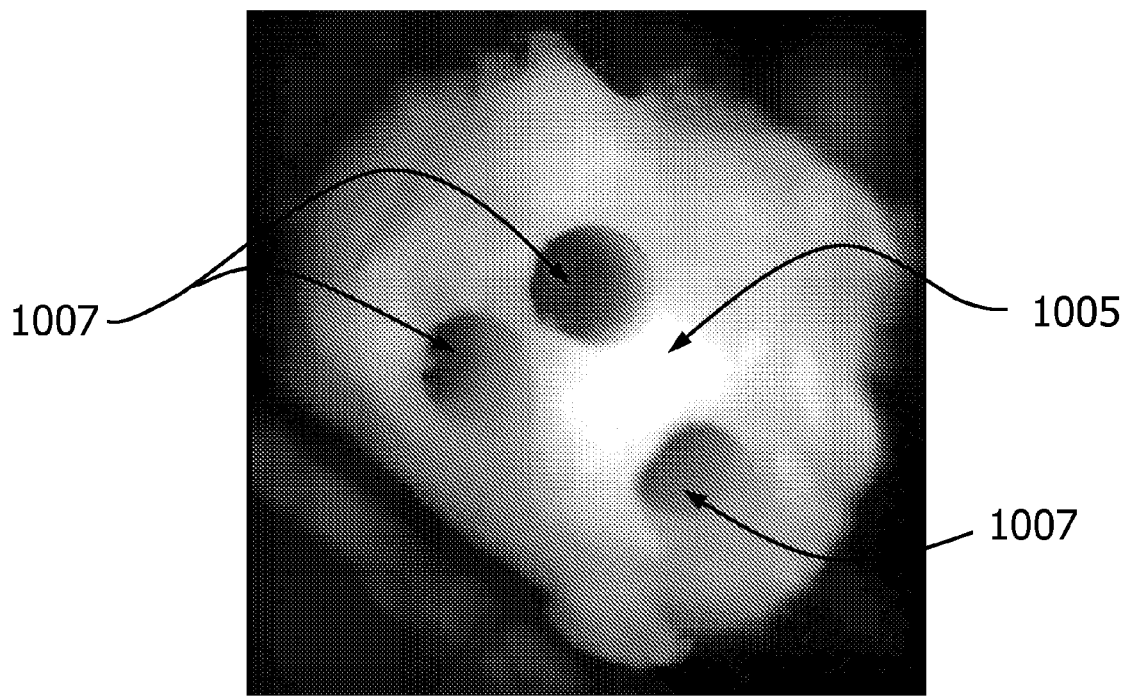
FIG. 7 is a photograph of a transverse section of one embodiment of an axon-guiding graft engineered according to the methods described herein, wherein the Schwann cells have been fluorescently labeled.

To visualize cellular arrangement within the mature axon-guiding graft, Schwalm cells were stained with fluorescent membrane dye, $DiIC_{18}(5)$-DS lipophilic carbocyanine tracer. These fluorescently labeled Schwann cells were used to create the mixed BMSC/Schwann cell multicellular bodies using the procedure outlined above, and the resulting mixed BMSC/fluorescently labeled Schwann cell multicellular bodies were used to prepare axon-guiding grafts according to the procedures outlined above. Following a ten day maturation period, the axon-guiding graft was removed from the agarose. Transverse sections were excised from the mature axon-guiding graft and observed using a fluorescent stereomicroscope to visualize the fluorescent staining and localization of the Schwann cells As can be seen in FIG. 7, the Schwann cells (represented by the brighter areas in the structure) are more concentrated in the central portion 1005 of the bioengineered axon-guiding graft and less concentrated at the periphery. Thus, it is recognized that the cells forming the central portion include a higher percentage of Schwann cells than the cells forming the peripheral portion of the graft. The three acellular channels 1007 in the structure appear as darker spots in the image. A color version of this photograph, showing the Schwann cells in green, appears as FIG. 2(a) of U.S. Provisional Application No. 61/337,307, which is incorporated by reference herein in its entirety and to which the present application claims priority. In converting the color photograph which appears in the provisional application and the Hubbard et al. reference to the black-and-white photograph presented as FIG. 7 herein, first, the color saturation of the entire image was increased, the brightness of the entire image was then increased, the image was converted to greyscale, and the contrast of the entire image was then increased. This process lightens the green fluorescent part of the graft and causes Schwann cell rich portions of the graft to appear lighter while other parts of the graft are a darker grey in the enhanced greyscale photograph.

This arrangement, wherein the Schwann cells are more concentrated in the central portion of the axon-guiding graft and less concentrated at the periphery, is illustrated schematically in FIG. 5. In FIG. 5, the outer peripheral portion 1003 has a lower concentration of Schwann cells as compared to the central portion 1005, which has a higher concentration of Schwann cells and contains the acellular channels 1007.

Example 4

Implantation of the Axon-guiding Graft in a Rat—Procedure 1

Regeneration of axons through the axon-guiding graft has been studied in a rodent sciatic nerve injury model. Female Sprague Dawley rats weighing approximately 400 grams were anesthetized with a mixed solution of ketamine (87 mg/kg) and xylazine (13 mg/kg) via an intraperitoneal (IP) route. The procedures were performed under sterile preparation and draping conditions and a warming pad was used during the procedure and upon recovery. Rats were kept in single cages pre- and postoperatively until completely sternal. Following sedation, the left lateral thigh of the rat was shaved and the rat hind limb was prepped and draped sterilely. Skin incisions were made with the scalpel along the mid lateral thigh and the skin flaps elevated exposing the muscle fascia. This was incised and the interval between the thigh musculature was split longitudinally, sharply exposing the direct course of the sciatic nerve at and distal to its branching point. A 1 cm stretch of the nerve proximal to its bifurcation was isolated and a 1 cm nerve segment was resected. The bioengineered axon-guiding graft was floated onto the field and secured as an interposition nerve graft at each end with fibrin glue, and allowed time to form a seal. The wound was irrigated gently and hemostasis achieved throughout the procedure with mild pressure. The muscle and skin were closed with 4-0 absorbable sutures. The rats were allowed to recover to a sternal condition on a warming pad in an isolated cage. FIG. 8 is a photograph of the surgical field in a rat following implantation of an axon guiding graft using this procedure. The axon-guiding graft 1001 can be seen in the surgical field 1009.

Example 5

Implantation of the Axon-guiding Graft in a Rat—Procedure 2

Female Sprague Dawley rats weighing approximately 400 grams were anesthetized with a mixed solution of ketamine (87 mg/kg) and xylazine (13 mg/kg) via an IP route. The procedures were performed under sterile preparation and draping conditions and a warming pad was used during the procedure and upon recovery. Rats were kept in single cages pre- and postoperatively until completely sternal. Following sedation, the left lateral thigh of the rat was shaved and the rat hind limb was prepared and draped sterilely. Skin incisions were made with the scalpel along the mid lateral thigh and the skin flaps elevated exposing the muscle fascia. This was incised and the interval between the thigh musculature was split longitudinally, sharply exposing the direct course of the sciatic nerve at and distal to its branching point. A 1 cm stretch of the nerve proximal to its bifurcation was isolated and a 1 cm nerve segment was resected. The bioengineered axon-guiding graft was floated into a longitudinally cut commercially available collagen nerve guide (i.e., a "collagen tube" or "collagen conduit") cut to fit the 1 centimeter wound (i.e., approximately 12 to 14 millimeters in length), which was used as a support sleeve for the engineered graft. The free ends of the native sciatic nerve were entubulated into the collagen support sleeve and secured with 9-0 nylon. The wound was then irrigated and hemostasis achieved with gentle pressure. The muscle and skin were closed with 4-0 absorbable sutures. The rats were allowed to recover to a sternal condition on a warming pad in an isolated cage.

Figure 9:
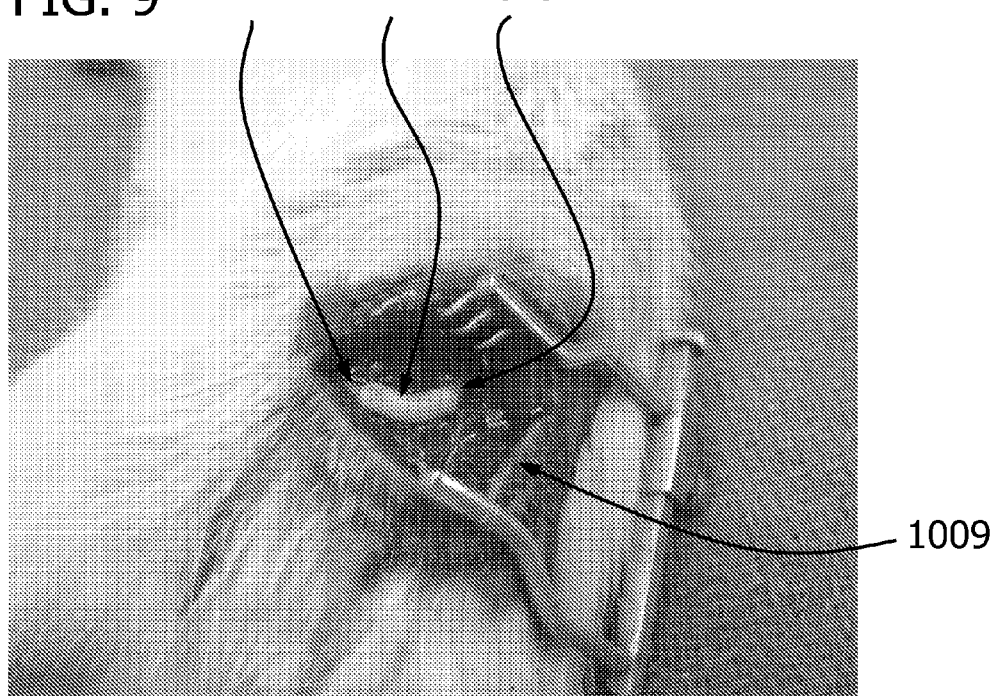

FIG. 9 is a photograph of the surgical field 1009 in a rat following implantation of an axon guiding graft inside of a collagen conduit 1011 using this procedure. The proximal 1013 and distal 1015 portions of the native nerve structure are also visible.

Example 6

Figure 10:
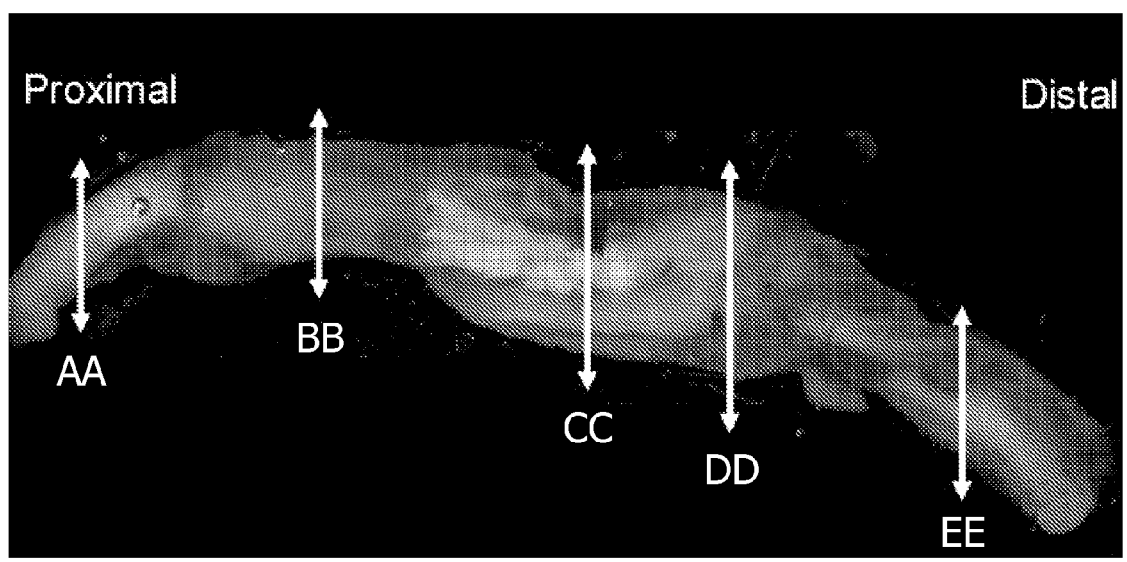
FIG. 10 is a photograph of a nerve segment containing one embodiment of an axon-guiding graft engineered according to the methods described herein which was harvested three weeks after implantation into a rat.

Gross Morphology and Histological Evaluation of the Axon-guiding Graft Three Weeks after Implantation At three-weeks post-implantation, rats were anesthetized in the same manner as described above and the implantation site exposed. Nerve segments comprising the bioengineered axon-guiding grafts and portions of the native nerve proximal and distal to the axon-guiding grafts were harvested from the rats and photographed for morphological observations. FIG. 10 is a photograph of a nerve segment containing an axon-guiding graft which was harvested three weeks after implantation using Procedure 2 as described above. The arrows in FIG. 10 indicate the locations where transverse sections were taken for histological evaluation. Section AA cuts at the proximal native nerve; Section BB at the proximal native nerve junction with the axon-guiding graft; Section CC at the center of the axon-guiding graft; Section DD at the distal axon-guiding graft junction with the native distal nerve; and Section EE at the native distal nerve. Any axons existing in the distal native nerve (i.e., at Section EE) have regenerated through the axon-guiding graft.

FIG. 11 shows histological images of transverse sections taken from locations corresponding approximately to the sections indicated by the arrows in FIG. 10, under 4× and 10× magnification. For histochemistry, the harvested nerve segments were fixed overnight in 4% paraformaldehyde. After dehydration with an ethanol series, tissues were processed for paraffin infiltration and embedding. 4 µm transverse sections were excised at the locations indicated in FIG. 10 and subjected to Bielschowsky staining to detect axons.

In FIG. 11, the axons 1017 appear as small black spots in the higher magnification (i.e., 10×) sections. In addition, a portion of the collagen support sleeve 1011 can be seen in some of the lower magnification (i.e., 4×) images. The white areas within the sections are the remaining portions of the acellular channels 1007. These histological images of the serial sections demonstrate the regeneration of axons from the proximal native nerve, through the axon-guiding graft, and into the distal native nerve.

FIG. 12 shows histological images taken at 40× magnification of transverse sections taken from the proximal native nerve and from the distal native nerve following a three-week implantation with a bioengineered axon-guiding graft inside a collagen conduit used as a support sleeve. The scale bar 1019 in FIG. 12 is 100 µm long. The axons 1017 appear as small black spots, and the images show that after a three-week implantation, about 40% of the axons present in the proximal stump crossed the bioengineered axon-guiding graft and reached the distal stump of the native nerve, as manually counted on high-magnification images.

Example 7

Gross Morphology of the Axon-guiding Graft Twelve Weeks after Implantation

A 10 mm resection was performed on the sciatic nerve of female Sprague Dawley rats in accordance with the procedures described above. A comparative study was carried out by repairing the gap with collagen conduits/sleeves which were either empty or filled with a bioengineered axon-guiding graft prepared using the methods described above. After twelve weeks, the collagen conduits (meaning the collagen conduit that was empty when implanted and the collagen conduit that was used as sleeve for the bioengineered graft) were harvested together with the proximal and distal nerve stumps, and photographed for morphological observations.

Figure 13:
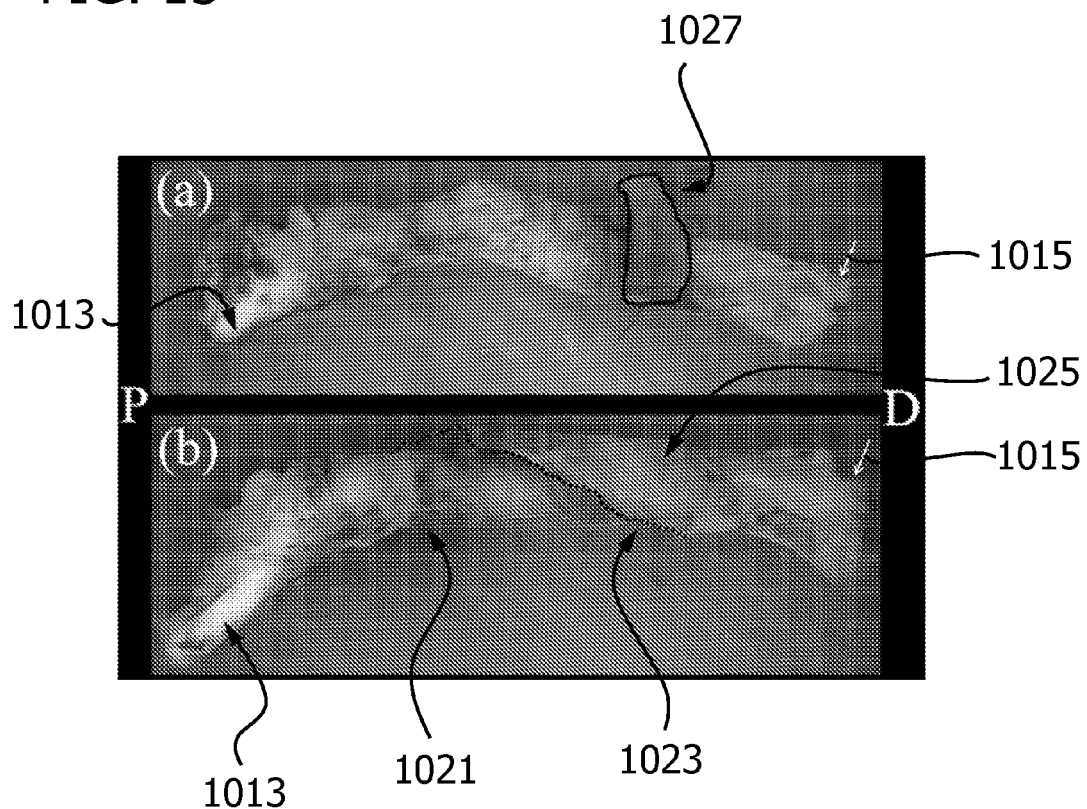
FIG. 13 is a photograph illustrating the gross morphology of nerve segments excised from rats following a 12-week implantation with a collagen conduit alone (panel (a)) or with a collagen conduit filled with an axon-guiding graft engineered according to the methods described herein (panel (b)).

FIG. 13 shows a comparison of the conduits and proximal and distal nerve stumps harvested following a 12-week implantation with a collagen conduit alone (panel (a)) or with a collagen conduit filled with a bioengineered axon-guiding graft (panel (b)). The proximal native nerve structures 1013 are visible on the far left ends of the harvested segments. The distal nerve structures 1015 are mostly surrounded by tissues, but are visible at the far right ends of the harvested segments. In panel (b), a portion of the collagen conduit has been removed to expose the smooth and well-defined repair 1021. The border of the cut in the collagen conduit is indicated by the dotted line 1023. The remains of the collagen conduit 1025 are to the right of the dotted line. The photographs indicate that after a 12-week implantation, continuity between the proximal and distal stumps of the nerve was reestablished using either method of repair. However, the collagen conduit containing the axon-guiding graft produced a smoother and better defined (i.e. constant diameter) connection. In addition, the collagen conduit implanted with the axon-guiding graft was almost completely intact; when the collagen conduit was implanted alone, on the other hand, it was almost totally resorbed. In panel (a) of FIG. 13, the only remaining portion of the collagen conduit is encircled by a solid line 1027. Without being bound to any particular theory, this is thought to be due to a decreased inflammatory response in the animals wherein the collagen conduit was implanted together with the axon-guiding graft, since the BMSCs have anti-inflammatory properties.

Example 8

Method of Repairing Severed Human Nerve

A human patient with a nerve in need of repair is identified. Nerve resection surgery is optionally performed on the patient. An axon-guiding graft having a length approximately equal to the distance between the proximal stump and distal stumps of the nerve to be repaired is prepared according to the procedures outlined above.

The human patient is anesthetized. The severed nerve is exposed and visualized using standard surgical techniques known in the art. An axon guiding graft is placed between the proximal and distal stumps of the nerve, and the proximal and distal stumps of the nerve are secured to the graft with sutures or a surgical adhesive. The wound is then irrigated and hemostasis achieved with gentle pressure. The muscle and skin are closed using standard surgical techniques known in the art.

Example 9

Method of Repairing Severed Human Nerve

A human patient with a nerve in need of repair is identified. Nerve resection surgery is optionally performed on the patient. An axon-guiding graft having a length approximately equal to the distance between the proximal stump and distal stumps of the nerve to be repaired is prepared according to the procedures outlined above.

The human patient is anesthetized. The nerve to be repaired is exposed and visualized using standard surgical techniques known in the art. An axon-guiding graft is floated into a longitudinally cut collagen support sleeve cut to fit the space between the proximal stump of the nerve and the distal stump of the nerve. Excess ends of the collagen support sleeve and/or graft can be removed if present. The proximal and distal ends of the nerve are entubulated into the collagen support sleeve and secured with sutures or a surgical adhesive. The wound is then irrigated and hemostasis achieved with gentle pressure. The muscle and skin are closed using standard surgical techniques known in the art.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

When introducing elements of the multicellular constructs, three-dimensional structures, axon-guiding grafts, and multicellular bodies herein, the articles "a", "an", "the" and "said" are intended to mean that there are one or more of the elements. The terms "comprising", "including" and "having" and variations thereof are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A multicellular construct consisting essentially of: a multicellular region comprising:
    a plurality of living cells cohered to one another to form an elongate graft for restoring neural connection between the ends of a severed nerve;
    a plurality of acellular channels extending axially through the multicellular region;
    and wherein the multicellular construct does not comprise any scaffold material at the time of implantation into a living organism having a nervous system.

2. The multicellular construct of claim 1 wherein the acellular channels are hollow or filled with one or more acellular materials.

3. The multicellular construct of claim 1 wherein the acellular channels are hollow, partially filled with one or more acellular materials, fully filled with one or more acellular materials, or any combination thereof.

4. The multicellular construct of claim 1 wherein the living cells comprise Schwann cells.

5. The multicellular construct of claim 4 wherein between about 0.1 and about 20 percent of the total number of living cells in the multicellular region are Schwann cells.

6. The multicellular construct of claim 5 wherein between 1 percent to about 10 percent of the total number of living cells in the multicellular region are Schwann cells.

7. The multicellular construct of claim 6 wherein between about 5 percent to about 10 percent of the total number of living cells in the multicellular region are Schwann cells.

8. The multicellular construct of claim 4 wherein the graft has a central portion and a peripheral portion surrounding the central portion, the percentage of cells in the central portion that are Schwann cells being higher than the percentage of cells in the peripheral portion that are Schwann cells.

9. The multicellular construct of claim 1 wherein the number of acellular channels is in the range of two to five.

10. The multicellular construct of claim 1 wherein the graft is tubular.

11. The multicellular construct of claim 1 wherein the graft is an engineered tissue.

12. The multicellular construct of claim 1 wherein the graft is non-innervated.

13. The multicellular construct of claim 1 wherein the graft comprises tissue culture medium.

14. An elongate three-dimensional structure comprising:
    a plurality of engineered multicellular bodies, each multicellular body comprising a plurality of living cells cohered to one another; and
    a plurality of discrete filler bodies, each filler body comprising a biocompatible material that resists migration and ingrowth of cells from the multicellular bodies into the filler bodies,
    wherein the multicellular bodies are arranged in a pattern in which each multicellular body contacts at least one other multicellular body and the filler bodies are positioned and arranged to form a plurality of acellular channels extending between opposite ends of the structure.

15. The multicellular construct of claim 1 wherein the acellular channels are hollow.

16. The elongate three-dimensional structure of claim 14 wherein the acellular channels have a side-by-side orientation to one another and are separated from one another by the multicellular bodies.

17. The elongate three-dimensional structure of claim 14 wherein there are at least three acellular channels extending between the opposite ends of the structure.

18. The elongate three-dimensional structure of claim 14 wherein the plurality of living cells comprises Schwann cells.

19. The elongate three-dimensional structure of claim 14 wherein at least some of the multicellular bodies or some of the filler bodies are substantially rod shaped.

20. The elongate three-dimensional structure of claim 14 wherein at least some of the multicellular bodies or some of the filler bodies are substantially spherical.

21. The multicellular construct of claim 1 for restoring nerve function by promoting regenerative axon growth through the graft when the graft is implanted in a living organism having a nervous system and positioned in a gap between the ends of a severed nerve, wherein the plurality of acellular channels extends between opposite ends of the multicellular region.

22. The multicellular construct of claim 21 wherein the acellular channels are hollow, partially filled with one or more acellular materials, fully filled with one or more acellular materials, or any combination thereof.

23. The multicellular construct of claim 21 wherein the living cells comprise Schwann cells.

24. The multicellular construct of claim 1, wherein the plurality of acellular channels extends axially through the interior of the multicellular region.

25. A multicellular construct as recited in claim 21, wherein the multicellular construct is an engineered tissue.

26. A multicellular construct as recited in claim 21 wherein the acellular channels have a side-by-side orientation to one another and are separated from one another by living cells in the multicellular construct.

\* \* \* \* \*

UNITED STATES PATENT AND TRADEMARK OFFICE
CERTIFICATE OF CORRECTION

PATENT NO. : 8,747,880 B2
APPLICATION NO. : 13/020000
DATED : June 10, 2014
INVENTOR(S) : Forgacs et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
Eleventh Day of August, 2015

Michelle K. Lee
*Director of the United States Patent and Trademark Office*